United States Patent
Yoon et al.

(10) Patent No.: US 9,861,501 B2
(45) Date of Patent: Jan. 9, 2018

(54) WALK-ASSISTIVE ROBOT AND METHOD OF CONTROLLING THE SAME

(71) Applicant: Samsung Electronics Co., Ltd., Suwon-Si, Gyeonggi-Do (KR)

(72) Inventors: Suk June Yoon, Seoul (KR); Kyung Shik Roh, Seongnam-si (KR); Young Bo Shim, Seoul (KR); Young Do Kwon, Yongin-si (KR); Sung Hwan Ahn, Seongnam-si (KR); Hyo Seok Hwang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 135 days.

(21) Appl. No.: 14/471,748

(22) Filed: Aug. 28, 2014

(65) Prior Publication Data
US 2015/0134079 A1    May 14, 2015

(30) Foreign Application Priority Data

Nov. 8, 2013    (KR) .......................... 10-2013-0135777

(51) Int. Cl.
*G06F 19/00*    (2011.01)
*A61F 2/68*    (2006.01)
(Continued)

(52) U.S. Cl.
CPC ................. *A61F 2/68* (2013.01); *A61F 2/60* (2013.01); *A61H 1/024* (2013.01); *A61H 1/0244* (2013.01);
(Continued)

(58) Field of Classification Search
CPC ...... A61F 2/60; A61F 2/66; A61F 2/68; A61F 2/6607; A61H 1/024; A61H 1/0244; A61H 1/0266; A61H 3/00; A61H 2003/001; A61H 2003/007; A61H 2201/5007; A61H 2201/5058; A61H 2201/5061; A61H 2201/5092; G05B 2219/40305;
(Continued)

(56) References Cited

U.S. PATENT DOCUMENTS

| | | | |
|---|---|---|---|
| 7,645,246 B2 * | 1/2010 | Rastegar | A61H 3/00 482/2 |
| 8,500,823 B2 * | 8/2013 | Herr | A61F 2/64 623/24 |

(Continued)

FOREIGN PATENT DOCUMENTS

| KR | 100917377 B1 | 9/2009 |
|---|---|---|
| KR | 100927335 B1 | 11/2009 |

OTHER PUBLICATIONS

European Search Report dated Jun. 15, 2015 for EP Application No. 14 19 1907.

*Primary Examiner* — Rachid Bendidi
(74) *Attorney, Agent, or Firm* — Harness, Dickey & Pierce, P.L.C.

(57) ABSTRACT

Provided are a walk-assistive robot and a method of controlling the same. The method of controlling the walk-assistive robot includes: obtaining ground information that is information regarding ground a walking direction; determining control patterns of the walk-assistive robot by analyzing the obtained ground information; and controlling the walk-assistive robot based on the determined control patterns.

13 Claims, 24 Drawing Sheets

(51) Int. Cl.
*A61H 3/00* (2006.01)
*A61F 2/60* (2006.01)
*A61H 1/02* (2006.01)

(52) U.S. Cl.
CPC ............. *A61H 3/00* (2013.01); *A61H 1/0266* (2013.01); *A61H 2003/001* (2013.01); *A61H 2003/007* (2013.01); *A61H 2201/5007* (2013.01); *A61H 2201/5058* (2013.01); *A61H 2201/5061* (2013.01); *A61H 2201/5092* (2013.01); *G05B 2219/40305* (2013.01); *Y10S 901/01* (2013.01); *Y10S 901/47* (2013.01)

(58) Field of Classification Search
CPC ..... Y10S 901/01; Y10S 901/47; B25J 13/085; B25J 19/0091; B25J 19/022; B25J 19/023; B25J 19/025; G05D 1/0248; G05D 2201/0217
USPC ......... 700/245–264; 701/23; 623/24, 27, 47, 623/53, 55; 180/8.1, 8.6; 318/568.12
See application file for complete search history.

(56) References Cited

U.S. PATENT DOCUMENTS

| | | | |
|---|---|---|---|
| 8,512,415 B2* | 8/2013 | Herr | A61F 2/60 623/24 |
| 8,619,082 B1* | 12/2013 | Ciurea | H04N 13/0022 345/427 |
| 9,097,538 B1* | 8/2015 | Bush | G01C 21/26 |
| 2004/0158355 A1* | 8/2004 | Holmqvist | G05D 1/0236 700/245 |
| 2006/0046909 A1* | 3/2006 | Rastegar | A63B 69/0028 482/91 |
| 2008/0027591 A1* | 1/2008 | Lenser | G05D 1/0251 701/2 |
| 2010/0094188 A1 | 4/2010 | Goffer et al. | |
| 2010/0114329 A1* | 5/2010 | Casler | B25J 19/0008 623/24 |
| 2010/0238161 A1 | 9/2010 | Varga et al. | |
| 2010/0245169 A1* | 9/2010 | O'Connor | G01C 21/20 342/357.25 |
| 2011/0004322 A1 | 1/2011 | Sankai | |
| 2011/0040216 A1 | 2/2011 | Herr et al. | |
| 2011/0054778 A1* | 3/2011 | Poiesz | G01C 21/3635 701/533 |
| 2011/0169923 A1* | 7/2011 | Dellaert | G06T 7/2033 348/47 |
| 2011/0264015 A1 | 10/2011 | Endo | |
| 2013/0107010 A1 | 5/2013 | Hoiem et al. | |
| 2013/0237884 A1 | 9/2013 | Kazerooni et al. | |
| 2014/0276262 A1* | 9/2014 | Kare | A61H 1/024 601/34 |
| 2015/0057801 A1* | 2/2015 | Stephens, Jr. | B25J 9/1689 700/259 |
| 2015/0197008 A1* | 7/2015 | Yoon | B25J 9/0006 700/250 |
| 2016/0368149 A1* | 12/2016 | Inaba | B25J 5/005 |
| 2017/0010620 A1* | 1/2017 | Watabe | G05D 1/0248 |

\* cited by examiner

WALK-ASSISTIVE ROBOT AND METHOD OF CONTROLLING THE SAME

CROSS-REFERENCE TO RELATED APPLICATION

This application claims the benefit of Korean Patent Application No. P2013-135777, filed on Nov. 8, 2013 in the Korean Intellectual Property Office, the disclosure of which is incorporated herein by reference.

BACKGROUND

1. Field

Example embodiments relate to a walk-assistive robot and a method of controlling the walk-assistive robot.

2. Description of the Related Art

Walk-assistive apparatuses are apparatuses that assist a user in performing the act of walking. The user may have trouble walking for various reasons including weak leg muscular strength due to, for example, an innate reason such as a genetic defect, or for an acquired reason such as a disease or an accident.

Walk-assistive apparatuses may include walk-assistive cars and walk-assistive robots. In walk-assistive cars, a rotation unit and a support for supporting a user are installed and the rotation unit and support are moved in response to a pushing force exerted by the user.

On the other hand, walk-assistive robots are fixed to a user's legs and supplement a shortage of force required for walking by applying the force required for walking to muscles. For example, the walk-assistive robot may be fixed to the user's thighs or shins and assist with motions of muscles and joints using various mechanical units, such as a motor, and the like, to assist the user in performing the act of walking. However, conventional walk-assistive robots may not anticipate a category of terrain before the walk-assistive robot encounters the terrain. Therefore, a conventional walking assistance robot may abruptly start and/or stop providing assistance to a wearer thereof.

SUMMARY

Example embodiments relate to a walk-assistive robot that is capable of recognizing a surrounding environment and rapidly responding to the surrounding environment, and a method of controlling the same.

Additional aspects of the example embodiments will be set forth in part in the description which follows and, in part, will be obvious from the description, or may be learned by practice of the example embodiments.

One or more example embodiments relates to a walk-assistive robot.

In one or more example embodiments, the walk-assistive robot may include: a ground data collecting unit configured to collect a plurality of pieces of ground data regarding ground; and a controller configured to create ground information regarding the ground based on the plurality of pieces of ground data, determine control patterns of the walk-assistive robot by analyzing the created ground information.

In one or more example embodiments, the walk-assistive robot may include: a ground information receiving unit configured to receive ground information; and a controller configured to determine control patterns of the walk-assistive robot by analyzing the received ground information and control the walk-assistive robot based on the determined control patterns.

In one or more example embodiments, the walking assistive robot is configured to assist a wearer thereof with walking. The walking assistive robot may include an assistance device having an exoskeleton structure configured to be worn on at least one leg of the wearer; at least one sensor configured to sense a terrain in at least a direction of the walking of the wearer; and a controller configured to control the assistance device based on the sensed terrain.

In one or more example embodiments, the at least one sensor includes an image capturing device configured to collect image data regarding the terrain.

In one or more example embodiments, the controller is configured to, determine a position and an orientation of the walking assistive robot by analyzing the image data using visual odometry, generate a three-dimensional (3D) map of the terrain, and classify the terrain into one of a plurality of categories based on the 3D map of the terrain.

In one or more example embodiments, the plurality of categories of terrain include terrain that is at least two of flat, inclined, stairs, and terrain having an obstacle thereon, and the controller is configured to classify the terrain by comparing at least two areas of the terrain in the 3D map thereof.

In one or more example embodiments, the 3D map includes information on a 2D plane of the terrain parallel to the walking direction and a height of the terrain, and the controller is configured to, classify the terrain as the flat terrain, if the 3D map indicates the at least two areas of the terrain have a same normal vector and a same height, classify the terrain as the inclined terrain, if the 3D map indicates that the at least two areas of the terrain have different normal vectors, and classify the terrain as the stairs, if the 3D map indicates that the two areas have a same normal vector and different heights.

In one or more example embodiments, the controller is configured to instruct the assistance device to provide greater assistance to the wearer if the terrain is classified as having the obstacle thereon, the inclined terrain or the stairs than if the terrain is classified as the flat terrain.

In one or more example embodiments, the at least one sensor includes an inertial measurement device configured to sense a change in speed and direction of the walking, and a ground reaction force sensor configured to detect a ground reaction force (GRF) transmitted to the wearer during the walking.

One or more example embodiments relates to a method of controlling a walk-assistive robot.

In one or more example embodiments, the method includes: obtaining ground information; determining control patterns of the walk-assistive robot by analyzing the obtained ground information; and controlling the walk-assistive robot based on the determined control patterns.

BRIEF DESCRIPTION OF THE DRAWINGS

These and/or other aspects of the example embodiments will become apparent and more readily appreciated from the following description of some example embodiments, taken in conjunction with the accompanying drawings of which.

DETAILED DESCRIPTION

Figure 1:
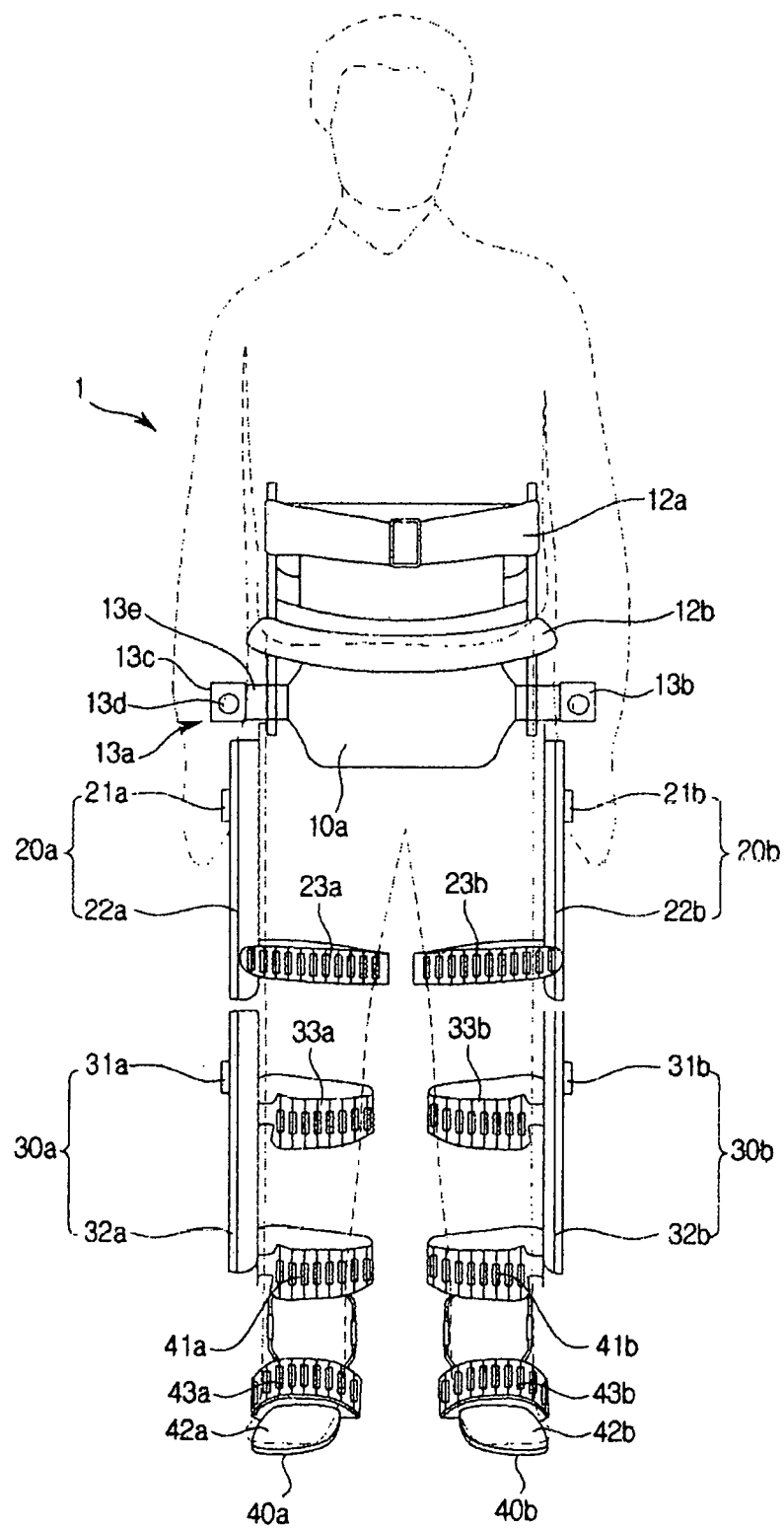
FIG. 1 is a front view of a walk-assistive robot in accordance with some example embodiments.

Reference will now be made in detail to some example embodiments, examples of which are illustrated in the accompanying drawings, wherein like reference numerals refer to like elements throughout.

Detailed illustrative example embodiments are disclosed herein. However, specific structural and functional details disclosed herein are merely representative for purposes of describing some example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIGS. 1 through 21 illustrate a walk-assistive robot that can be mounted on a user (e.g. a human body), as an example of a walk-assistive apparatus in accordance with example embodiments.

Figure 2:
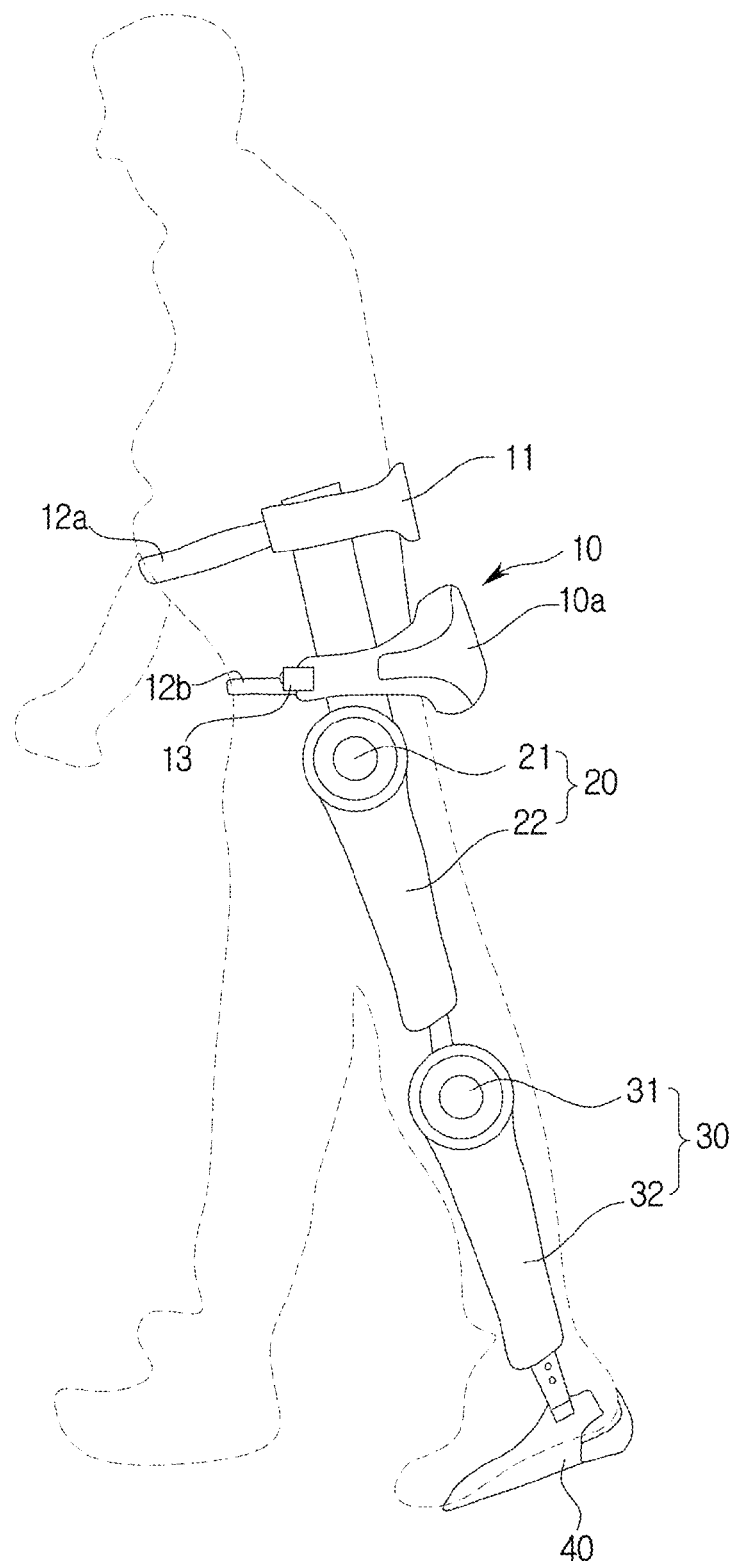
FIG. 2 is a side view of the walk-assistive robot illustrated in FIG. 1.
Figure 3:
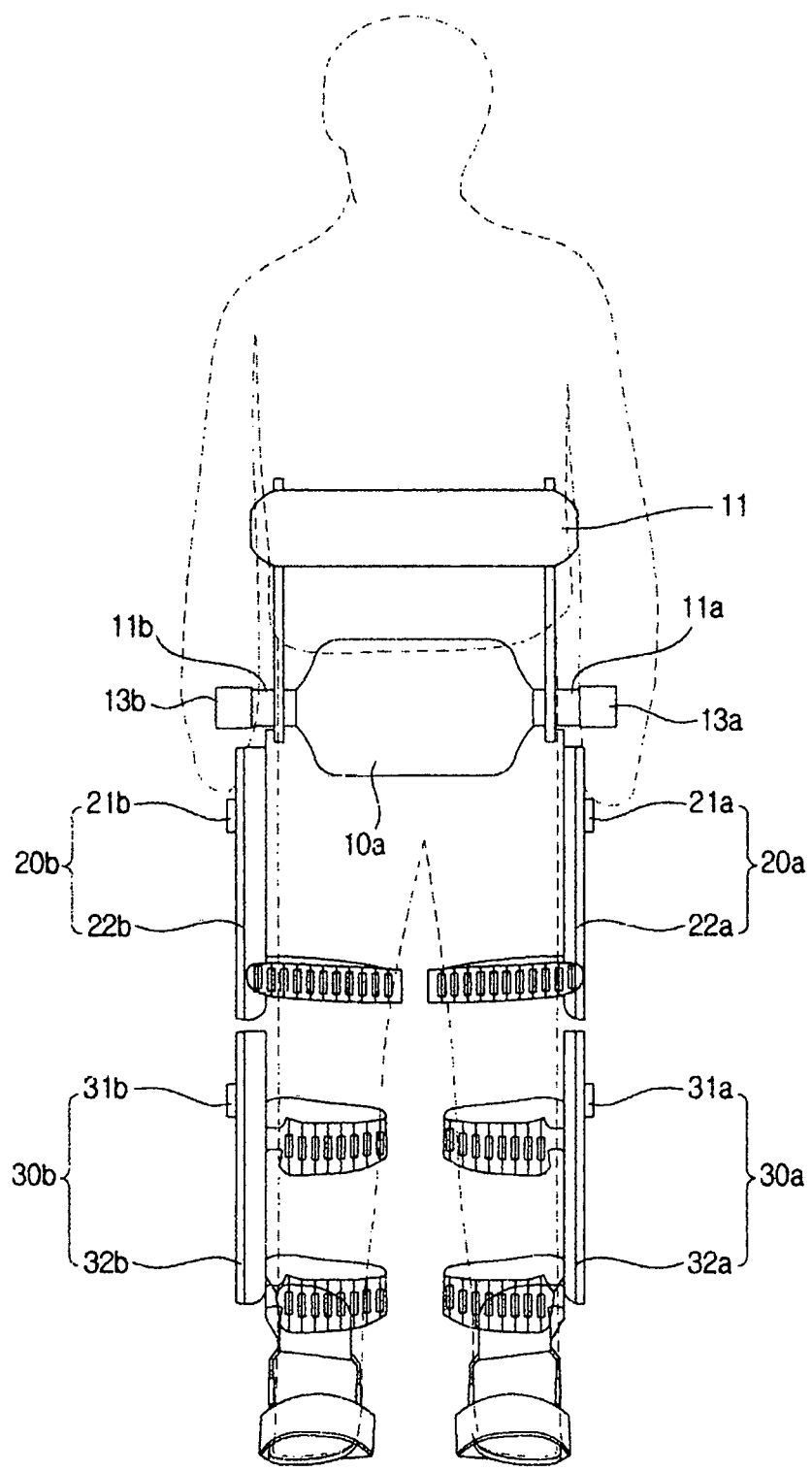
FIG. 3 is a rear view of the walk-assistive robot of FIG. 1.

FIGS. 1 through 3 are a front view, a side view, and a rear view of a walk-assistive robot in accordance with an example embodiment.

Referring to FIGS. 1 through 3, as illustrated in FIG. 2, a walk-assistive robot 1 may include a body 10 and walk-operating units 20, 30 and 40.

The body 10 may include a housing 10a in which various components can be embedded. The housing 10a may provide a function of safely protecting and safely fixing various embedded components. As discussed below, various processing units, such as central processing units (CPUs) or graphic processing units (GPUs), and a printed circuit board (PCB) may be embedded in one or more controllers installed in the housing 10a. Also, as discussed in more detail below, various storage units may also be embedded in the housing 10a as needed.

The controller installed in the housing 10a may include a processor. The processor may include a silicon chip in which an arithmetic operation logic operation unit, a digital signal processor, a microcomputer, a field programmable array, a programmable logic unit, a microprocessor, a register, a program counter, a command decoder, a control circuit or any other device capable of responding to and executing instructions in a defined manner is installed.

Figure 22:
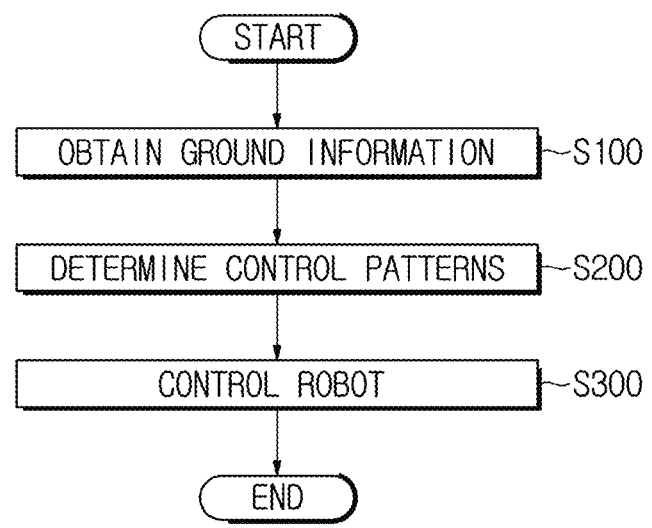
FIG. 22 is a flowchart illustrating a method of controlling a walk-assistive robot in accordance with some example embodiments.
Figure 23:
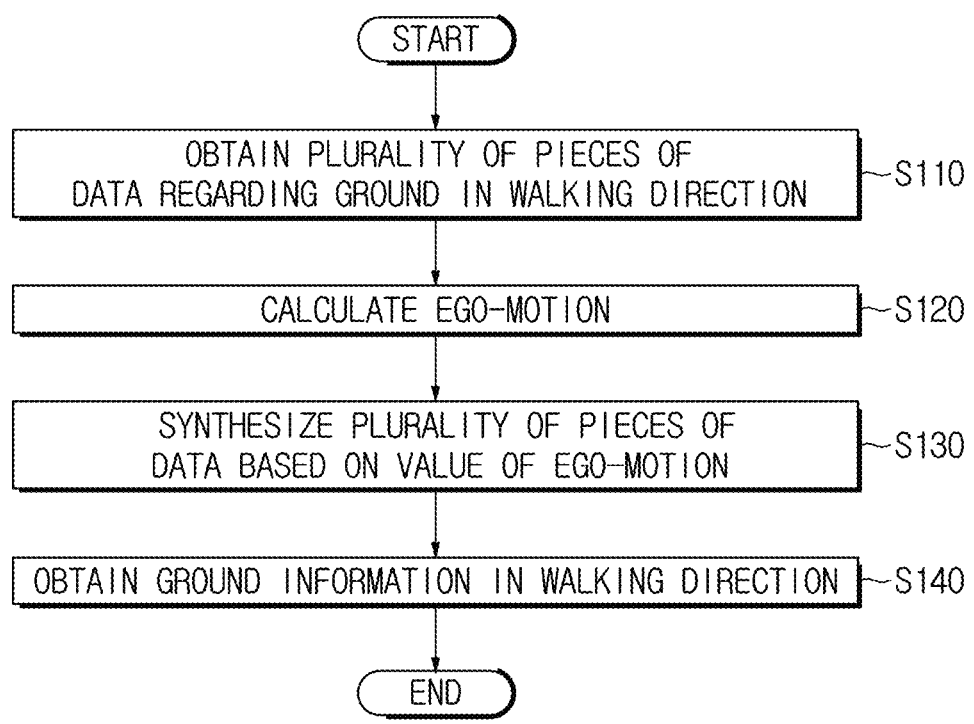
FIG. 23 is a flowchart illustrating a method of obtaining ground information in accordance with some example embodiments.
Figure 24:
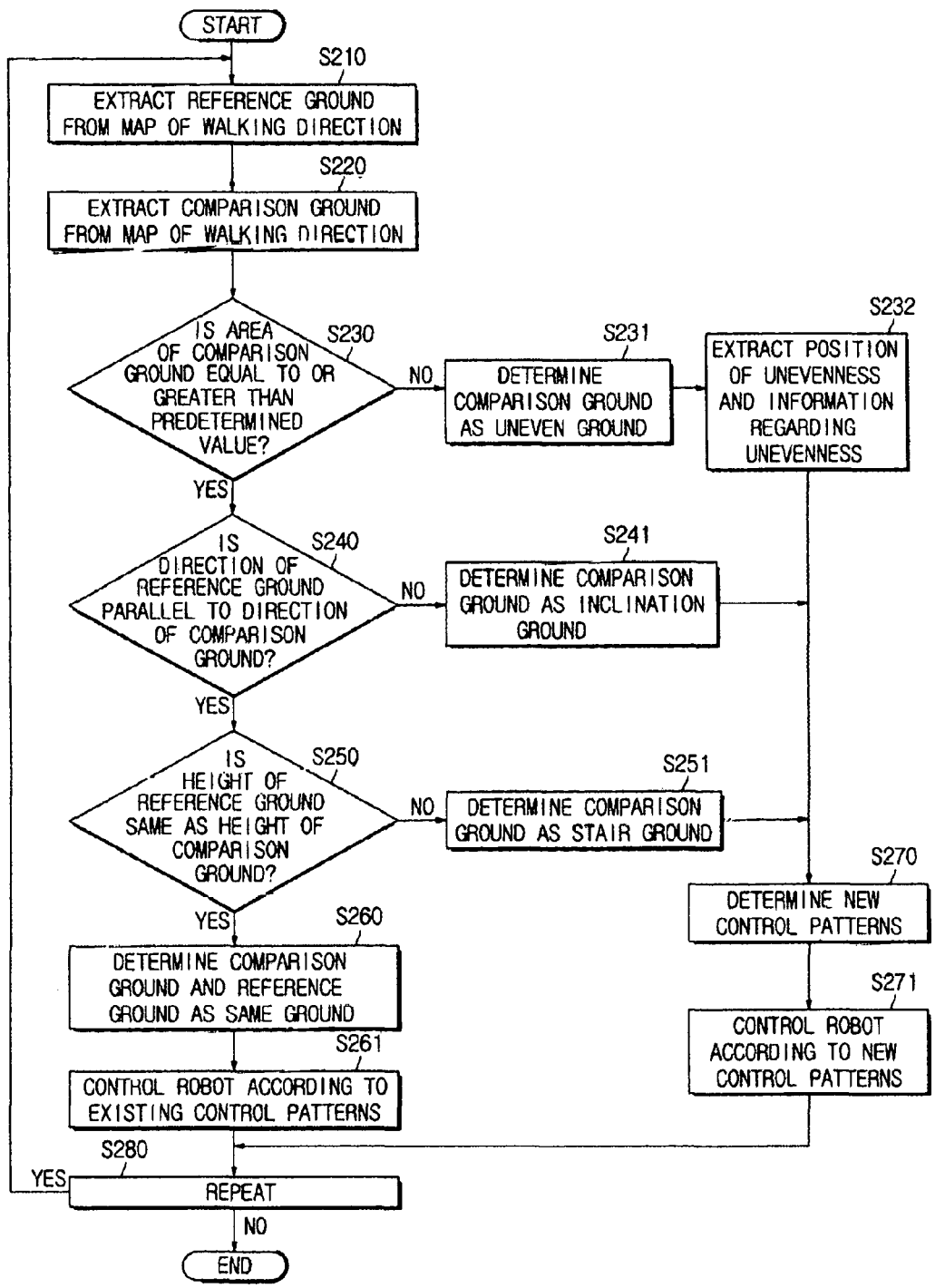
FIG. 24 is a flowchart illustrating a method of controlling a walk-assistive robot in accordance with other example embodiments.

The processor may be programmed with instructions that configure the processor as a special purpose computer to perform the operations illustrated in FIGS. 22 to 24, such that the controller 14 is configured to generate control signals for controlling operations of the walk-operating units 20 through 40 and may transmit the generated control signals to the walk-operating units 20 through 40. The controller may generate ground information based on ground data collected by a ground data collecting unit 13 according to some example embodiments and may also generate control signals according to the generated ground information.

The ground information may include information regarding unevenness or a shape of ground. The ground information may include information regarding the ground within a desired (or, alternatively, a predetermined) range of the walk-assistive robot 1. The ground information may also include information regarding the ground in a direction in which a wearer walks and/or information regarding the ground located behind or beside the wearer. According to some example embodiments, the ground information may be a map in a walking direction.

The graphic processing unit (GPU) is a processing unit that processes information regarding graphics. The GPU may assist the CPU with a graphic processing function or may perform graphic processing solely. The GPU may also perform image processing based on image data collected by the ground data collecting unit 13 according to an example embodiment. Also, the GPU may generate ground information based on the ground data collected by the ground data collecting unit 13.

The printed circuit board (PCB) is a board in which a circuit is printed, and on which the CPU, GPU and/or various storage units may be installed. The PCB may be fixed to an inner side surface of the housing 10a and may cause the CPU to be stably fixed to the PCB.

Various storage units may be embedded in the housing 10a. The storage unit may be a magnetic disk storage unit for storing data by magnetizing a surface of a magnetic disk or a semiconductor memory unit for storing data using various types of memory semiconductors. Ground information or ground data may also be stored in the storage unit. A power supply for supplying power to various components inside the housing 10a or the walk-operating units 20 through 40 may be further embedded in the housing 10a. Also, an actuator may be further installed at the housing 10a so as to control the operations of the walk-operating units 20 through 40 or to drive the walk-operating units 20 through 40.

According to some example embodiments, the body 10 may further include a waist support portion 11 for supporting the wearer's waist. The waist support portion 11 may have a shape of a curved flat plate so as to support the wearer's waist.

Also, the body 10 may further include one or a plurality of fixing units 12a and 12b so as to fix the housing 10a or the waist support portion 11 to the wearer. Various types of units for fixing the housing 10a to the wearer's waist or hip may be used as the plurality of fixing units 12a and 12b. For example, the fixing units 12a and 12b may be bands having elasticity or various types of straps.

The body 10 may include one or a plurality of ground data collecting units 13 that collect a plurality of pieces of ground data regarding the ground. For example, the ground data collecting unit 13 may be one or more sensors that collect information on the presence of an obstacle on the wearer's walking path or a change in the ground at a sufficiently time prior to the obstacle or change in the ground so that the walk-operating units 20, 30 and 40 may be properly controlled according to the presence of the obstacle or the change in the ground.

The ground data collecting unit 13 may collect ground data by collecting visible rays or infrared rays reflected from or generated by the ground. The ground data collecting unit 13 may also collect the ground data using rays, such as visible rays, infrared rays, or lasers, using electromagnetic waves, such as ultrashort waves or microwaves, or using ultrasonic waves.

The ground data collecting unit 13 may collect data regarding the ground within a desired (or, alternatively, a predetermined) range of the walk-assistive robot 1. For example, the ground data collecting unit 13 may collect data regarding ground located close to the wearer. According to some example embodiments, the ground data collecting unit 13 may also collect data regarding ground located distant from the wearer. According to some example embodiments, the ground data collecting unit 13 may collect data regarding the ground located forward in the wearer's walking direction. According to some example embodiments, the ground data collecting unit 13 may collect data regarding the ground located sideward or rearward from the wearer's walking direction. The range of collection of the ground data may be determined by a direction or a viewing angle of a camera or three-dimensional (3D) depth sensor of the ground data collecting unit 13. The range of collection of the ground data may be determined by a designer of the walk-assistive robot 1 or according to a user's selection.

According to some example embodiments, the ground data collecting unit 13 may be an image capturing unit, such as a camera that collects image data regarding the ground by transforming visible rays or infrared rays transmitted from an outside. For example, the camera may include at least one of a still image camera, a moving picture camera, a stereo camera, a panorama camera, and an infrared camera. In example embodiments in which the group data collecting unit 13 is an infrared camera, the ground data collected by the ground data collecting unit 13 may also include visible ray image data and infrared image data.

In other example embodiments, the ground data collecting unit 13 may be a 3D depth sensor. The 3D depth sensor may collect information regarding the ground using rays. For example, the 3D depth sensor may radiate infrared rays onto a subject, for example, onto the ground, may receive the infrared rays reflected from the subject and then may detect a shape or position of the subject based on the received infrared rays.

Various imaging units that may capture and collect an image as well as the above-described camera or sensor may be used as the ground data collecting unit 13.

The ground data collecting unit 13 may be installed at the housing 10a, as illustrated in FIGS. 1 through 3.

The ground data collecting unit 13 may protrude toward an outer side of the housing 10a and may be installed at the housing 10a. The ground data collecting unit 13 may also be installed at one or a plurality of sides of the housing 10a so as to easily collect the ground data of the housing 10a. Also, the ground data collecting unit 13 may be buried in the housing 10a and may be installed therein. If the ground data collecting unit 13 is buried in and installed in the housing 10a, an incision hole may be formed in an outer side of the housing 10a. A lens of the ground data collecting unit 13 may receive external light through the incision hole. In some example embodiments, a single ground data collecting unit 13 may be installed at the walk-assistive robot 1. In other example embodiments, a plurality of ground data collecting units 13a and 13b may be installed, as illustrated in FIG. 1.

When the ground data collecting unit 13 is installed at the outer side of the housing 10a, each of the ground data collecting units 13a and 13b may include a sensor housing 13c, a sensor 13d, and a rotation unit 13e.

The sensor 13d may be embedded in the sensor housing 13c, and the sensor housing 13c may provide a function of fixing and protecting the sensor 13d.

The sensor 13d may be an image capturing unit, such as a camera, or a 3D depth sensor, as described above.

The rotation unit 13e may connect the sensor housing 13c and the housing 10a and may simultaneously rotate the sensor housing 13c in one or a plurality of directions. The rotation unit 13e may include a bearing having a ball or roller. A type of the bearing may be determined in various ways according to a designer's selection. The rotation unit 13*e* may rotate automatically according to driving of a motor or a cylinder unit or may be rotated manually by the wearer.

According to some example embodiment, the ground data collecting unit 13 may face one or a plurality of directions among a front, a rear, and sides of the walking direction of the wearer. For example, the ground data collecting unit 13 may face forward in the walking direction so as to collect ground data regarding the ground located forward in the walking direction of the wearer or may face sideward or rearward from the walking direction so as to collect ground data regarding the ground located sideward or rearward from the walking direction of the wearer. Also, the ground data collecting unit 13 may collect data in a plurality of directions in relation to the wearer while the housing 10*a* of the ground data collecting unit 13 rotates around a desired (or, alternatively, a predetermined) rotation shaft, for example, the rotation unit 13*e*.

The body 10 may include one or a plurality of inertial measurement units (IMUs). An IMU may be installed at an inner side or outer side of the housing 10*a*, and more particularly, may be installed at a PCB that is fixed to an inner side of the housing 10*a*. The IMU may include at least one of an inertial sensor having a plurality of axes, for example, a triaxial inertial sensor and a gyro sensor. A control unit, such as the CPU of the body 10, may control the operations of the walk-operating units 20, 30 and 40 based on inertia measured by the IMU.

The walk-operating units 20, 30 and 40 may include a first structure portion 20, a second structure portion 30, and a third structure portion 40, as illustrated in FIGS. 1 through 3. The first structure portion 20 may assist with the wearer's thigh and hip joint movement in a walking operation. The second structure portion 30 may assist with the wearer's lower leg and knee joint movement in the walking operation. Also, the third structure portion 40 may assist with the wearer's ankle joint and associated muscle movement in the walking operation.

According to some example embodiments, the walk-assistive robot 1 may include one first structure portion 20, one second structure portion 30, and one third structure portion 40. In this case, the first structure portion 20, the second structure portion 30, and the third structure portion 40 may be worn at one of the wearer's left foot and right foot. Also, according to another embodiment, a pair of first structure portions 20, a pair of second structure portions 30, and a pair of third structure portions 40 may be worn on the wearer's left foot and right foot so as to assist both feet with walking (see 20*a*, 20*b*, 30*a*, 30*b*, 40*a*, and 40*b* of FIG. 1). Regardless of whether there are only one first structure portion 20, only one second structure potion 30 and only one third structure portion 40, or a plurality of first structure portions 20, a plurality of second structure portions 30 and a plurality of third structure portions 40, functions or operations of the first structure portion 20, the second structure portion 30, and the third structure portion 40 may be almost identical.

Hereinafter, for convenience of explanation, the walk-assistive robot 1 including a plurality of first structure portions 20, a plurality of second structure portions 30, and a plurality of third structure portions 40 will be described, however, example embodiments are not limited thereto.

First Structure Portion

The plurality of first structure portions 20*a* and 20*b* may include first driving portions 21*a* and 21*b* and first support portions 22*a* and 22*b*, respectively. Further, as discussed in more detail below, the plurality of first structure portions 20*a* and 20*b* may also include first fixing portions 23*a* and 23*b*, respectively.

The first driving portions 21*a* and 21*b* may generate rotational forces having various sizes while rotating. The rotational forces generated by the first driving portions 21*a* and 21*b* may be applied to the first support portions 22*a* and 22*b*. The first driving portions 21*a* and 21*b* may be set to drive the walk-assistive robot 1 by rotation within an operating range of a human's hip joint.

In some example embodiments, the first driving portions 21*a* and 21*b* may include a motor for generating a rotational force of a desired (or, alternatively, a predetermined) torque according to electrical energy supplied from the body 10. In some example embodiments, each of the first driving portions 21*a* and 21*b* may include a piston or cylinder unit that generates a rotational force by operating due to the electrical energy supplied from the body 10 or pressure of a fluid, for example, pressure such as hydraulic pressure or air pressure. According to some example embodiments, the first driving portions 21*a* and 21*b* may include the motor, the piston, and the cylinder unit.

At least one first support portion 22*a* or 22*b* may be physically connected to the first driving portions 21*a* and 21*b* and may be rotated in a desired (or, alternatively, a predetermined) direction according to the rotational forces generated by the first driving portions 21*a* and 21*b*.

The first support portions 22*a* and 22*b* may be implemented by one or a plurality of supports, as illustrated in FIGS. 1 through 3. The first support portions 22*a* and 22*b* may have various shapes as needed. For example, the first support portions 22*a* and 22*b* may have hexahedral shapes. The first support portions 22*a* and 22*b* may be implemented by a plurality of supports that are combined with one another.

Also, the first support portions 22*a* and 22*b* may be implemented in a shape in which a plurality of sections are connected to each other. In this case, a plurality of joints that connect the plurality of sections may be combined with the plurality of sections. The plurality of joints may be rotated in a desired (or, alternatively, a predetermined) direction. Thus, the first support portions 22*a* and 22*b* may be bent in a desired (or, alternatively, a predetermined) direction within a desired (or, alternatively a predetermined) range according to a range of rotation of the plurality of joints. Two sections of the plurality of sections may be connected to each other via one joint or the plurality of joints according to some example embodiments. When two sections are connected to each other via the plurality of joints, the plurality of joints may be rotated in different directions. Thus, the first support portions 22*a* and 22*b* may be bent in various directions within a desired (or, alternatively, a predetermined) range.

The first support portions 22*a* and 22*b* may be formed of a material having flexibility according to some example embodiments and may be bent due to flexibility of the material within a desired (or, alternatively, a predetermined) range.

The first fixing units 23*a* and 23*b* may fix the first support portions 22*a* and 22*b* to the wearer. For example, the first fixing units 23*a* and 23*b* may fix the first support portions 22*a* and 22*b* to the wearer's thighs. The first support portions 22*a* and 22*b* may be fixed to inner sides or outer sides of the wearer's thighs using the first fixing units 23*a* and 23*b*. If the first support portions 22*a* and 22*b* are rotated due to driving of the first driving portions 21*a* and 21*b*, the thighs to which the first support portions 22*a* and 22*b* are fixed may also cause the hip joint to be rotated in the same direction.

The first fixing units 23a and 23b may be formed of a metal material or various materials having elasticity, such as rubber. In some example embodiments, the first fixing units 23a and 23b may be chains, as illustrated in FIG. 1. In some example embodiments, the first fixing units 23a and 23b may be bands having elasticity or various straps. In addition, various fixing units for fixing the first support portions 22a and 22b to the wearer's thighs may also be used as the first fixing units 23a and 23b.

The first fixing portions 23a and 23b are fixed to the wearer's thighs so that the first structure portions 20a and 20b may apply a desired (or, alternatively, a predetermined) rotational force to the wearer's thighs or hip joint so as to assist the wearer with an operation of raising or lowering the thighs. Thus, when the wearer performs an operation of raising a leg or a walking operation, assistance can be provided to the wearer.

One or a plurality of inertial measurement units IMUs may be installed at the first structure portion 20. For example, the one or plurality of IMUs may be installed at the first driving portions 21a and 21b, the first support portions 22a and 22b, or at both the first driving portions 21a and 21b and the first support portions 22a and 22b.

Second Structure Portion

The second structure portion 30a, 30b may include a second driving portion 31a, 31b, a second support portion 32a, 32b, and a second fixing units 33a, 33b, as illustrated in FIGS. 1 through 3.

Second driving portions 31a and 31b may generate rotational forces having various sizes in a desired (or, alternatively, a predetermined) direction. The second driving portions 31a and 31b may be set to drive the walk-assistive robot 1 within an operating range of a human's knee joints.

In example embodiments, each of the second driving portions 31a and 31b may include a motor, a piston, or a cylinder unit that generates a rotational force of a desired (or alternatively, a predetermined) torque due to power supplied directly from the body 10 or pressure of a fluid or power supplied indirectly from the first structure portions 20a and 20b or pressure of a fluid. In some example embodiments, the second driving portions 31a and 31b may include all of the motor, the piston, and the cylinder unit, as described above.

At least one second support portion 32a or 32b may be physically connected to the second driving portions 31a and 31b and may be rotated in a desired (or, alternatively, a predetermined) direction according to the rotational forces generated by the second driving portions 31a and 31b. A configuration, a structure, and a material of each of the second support portions 32a and 32b may be the same as or different from those of the first support portions 22a and 22b.

The second fixing units 33a and 33b for fixing the second support portions 32a and 32b to the wearer's lower legs. The second support portions 32a and 32b may be fixed to the inner sides or outer sides of the wearer's thighs using the second fixing units 33a and 33b. A configuration, a structure, and a material of each of the second fixing units 33a and 33b may be the same as or different from those of the first fixing units 23a and 23b.

The lower legs can be fixed to the second support portions 32a and 32b via the second fixing units 33a and 33b so that the second structure portions 30a and 30b can apply desired (or alternatively, a predetermined) rotational forces to the wearer's lower legs or knee joints. Thus, the second structure portions 30a and 30b can assist the wearer's operation of raising or lowering the lower legs.

One or a plurality of IMUs may be installed at the second structure portion 30. In some example embodiments, the IMUs may be installed at the first structure portion 20 and the second structure portion 30. In other example embodiments, the IMUs may be installed at the second structure portion instead of the first structure portion 20.

Third Structure Portion

The third structure portion 40 may assist with the wearer's ankle movement in the walking operation. The third structure portion 40 may include third fixing units 41a and 41b, footrest portions 42a and 42b, and fourth fixing units 43a and 43b, as illustrated in FIG. 1.

The third fixing units 41a and 41b may be connected to the second support portions 32a and 32b and may provide a function of fixing the wearer's ankles to the second support portions 32a and 32b. A configuration, a structure, and a material of each of the third fixing units 41a and 41b may be the same as or different from those of the first fixing units 23a and 23b.

The footrest portions 42a and 42b may be mounted on the wearer's soles.

A desired (or, alternatively, a predetermined) pressure sensor may be installed at each of the footrest portions 42a and 42b. The pressure sensor may detect whether the wearer wears the walk-assistive robot 1 or stands by detecting the wearer's weight. The pressure sensor may be embodied as a ground reaction force (GRF) sensor for detecting a GRF transmitted to the wearer's feet when the wearer walks. The pressure sensor that detects weight and the GRF sensor that detects the GRF may be implemented as independent sensors or as one sensor as needed.

The fourth fixing units 43a and 43b may fix the wearer's feet onto the footrest portions 42a and 42b, thereby providing a function that enables the wearer to stably put his/her feet on the footrest portions 42a and 42b.

The third structure portion 40 may also include a driving unit, such as a motor or a cylinder. The driving unit of the third structure portion 40 may assist with the wearer's movement relating the ankle joint and muscles around the ankle.

One or a plurality of IMUs may also be installed at the third structure portion 40, as described above. In some example embodiments, one or a plurality of IMUs may be installed only at the third structure portion 40.

The number of fixing units 23a, 23b, 33a, 33b, 41a, 41b, 43a, and 43b included in the walk-assistive robot 1 may vary.

According to an example embodiment, driving and operations of the first through third structure portions 20 through 40 may be disclosed or controlled by the actuator installed at the body 10. Also, each of the first through third structure portions 20 through 40 may start separately and may operate due to separately transmitted control signals.

Through various components described above and their operations, the walk-assistive robot 1 may assist the user with walking.

Control of the Walk-Assistive Robot

Hereinafter, the configuration of the walk-assistive robot 1 for controlling the walk-operating unit 20, 30 and 40 of the walk-assistive robot 1 will be described with reference to FIGS. 4 through 21.

Figure 4:
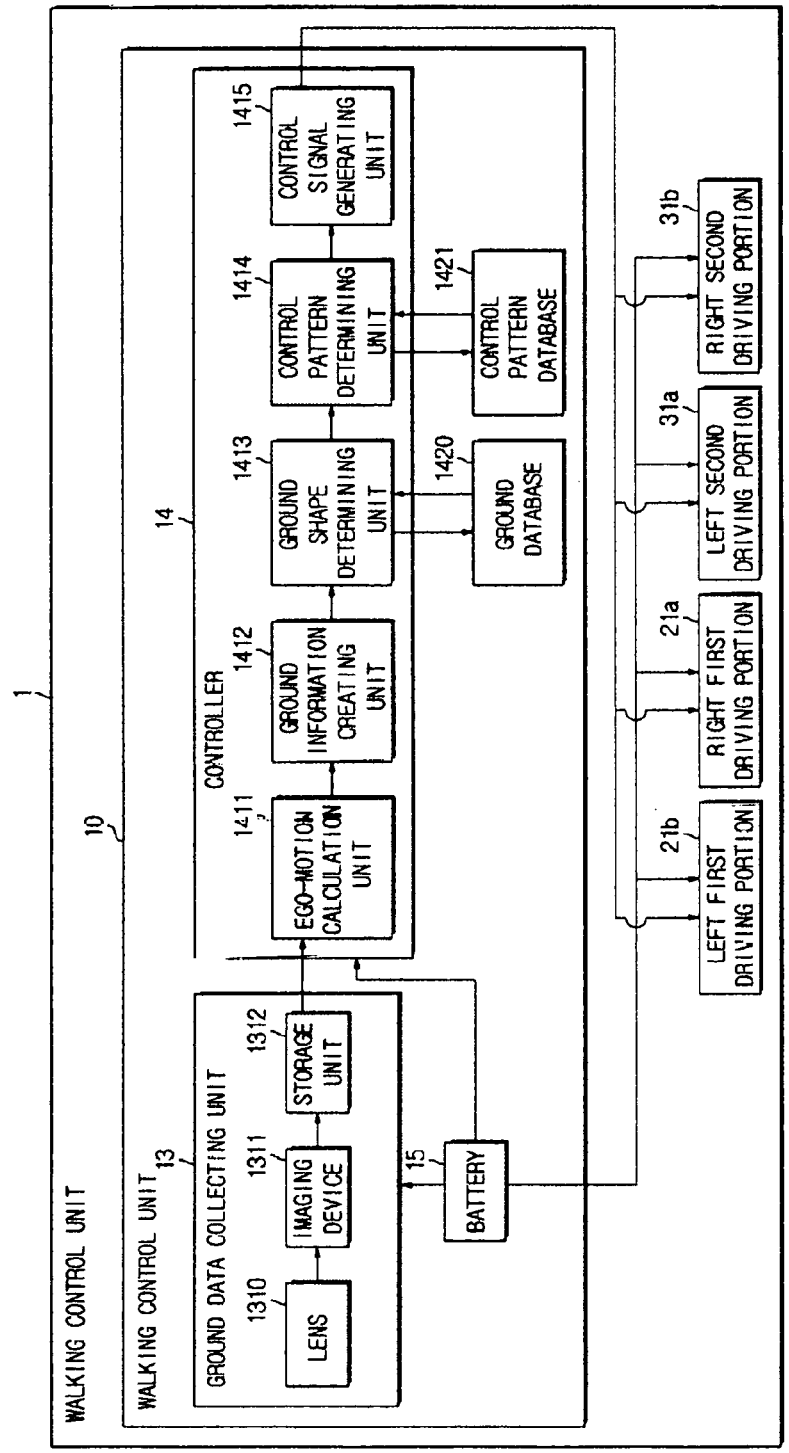
FIG. 4 illustrates a configuration of the walk-assistive robot of FIG. 1.

FIG. 4 illustrates a configuration of the walk-assistive robot 1 of FIG. 1

Referring to FIG. 4, the body 10 of the walk-assistive robot 1 may include a walking control unit. The walking control unit may include the ground data collecting unit 13 and a controller 14. The walk-assistive robot 1 may be controlled using the ground data collecting unit 13 and the controller 14. The ground data collecting unit 13 may obtain a plurality of pieces of ground data. The ground data collecting unit 13 may be installed at an outer side or inner side of the body 10, as described above, and may collect ground data from external ground.

The ground data collecting unit 13 may include a lens 1310, an imaging device 1311, and a storage unit 1312.

The lens 1310 may include at least one of a visible ray lens and an infrared lens and may receive visible rays and/or infrared rays that are radiated or reflected from an external object. The visible rays and/or infrared rays reflected from the external object may be generated by the ground data collecting unit 13 and may be radiated onto the external object.

The imaging device 1311 may convert the received visible rays and/or infrared rays into electrical signals corresponding to the received visible rays or infrared rays. The imaging device 1311 may be a charge coupled device (CCD) or a complementary metal-oxide semiconductor (CMOS). Also, the imaging device 1311 may be a Foveon sensor, etc. The type, number, or size of the imaging device 1311 may be selected according to the designer's need.

The electrical signals converted by the imaging device 1311 from the rays may be used as ground data immediately without additional processing. Alternatively, the electrical signals may be amplified or undergo an analog-digital conversion procedure. The electrical signals that undergo this procedure may also be used as the ground data.

The storage unit 1312 may store the ground data temporarily or permanently. Alternatively, in some example embodiments, the storage unit 1312 may be omitted.

The plurality of pieces of ground data regarding one or a plurality of directions among the front, the rear, and the sides of the walking direction of the wearer may be obtained by the ground data collecting unit 13. The obtained plurality of pieces of ground data may be transmitted to the controller 14, as illustrated in FIG. 4. For example, the ground data may be transferred from the storage unit 1312 to the controller 14.

The controller 14 may generate control instructions based on the electrical signals and then may control the walk-operating units 20, 30 and 40 based on the control instructions. The controller 14 may be implemented by the above-described CPU, a storage medium, such as a cache or buffer, and various circuits. Further, the controller 14 may be implemented using the GPU as needed.

The controller 14 may control the walk-assistive robot 1 by performing various arithmetic operations based on the data collected by the ground data collecting unit 13, create the control instruction according to a result of performing the arithmetic operation, and transmit the created control instruction to the walk-operating units 20, 30 and 40 to cause the walk-operating units 20 through 40 to assist the wearer with walking.

As discussed above, the controller 14 may be configured to execute machine executable code that configures the controller 14 as a special purpose computer to operate as an ego-motion calculation unit 1411 and a ground information creating unit 1412, as illustrated in FIG. 4. Further, as discussed in more detail below, the controller 14 may also be configured as a ground shape determining unit 1413, a control pattern determining unit 1414 and/or a control signal generating unit 1415.

Using the ego-motion calculation unit 1411 and the ground information creating unit 1412, the controller 14 may calculate an ego-motion, and generate ground information using the ground data (S120 through S140), as illustrated in FIG. 23.

Calculating Ego-Motion

The ego-motion is a motion of a sensor, such as a camera, within an environment. The environment may be rigid, such that the ego-motion may refers to estimating a sensor's motion relative to the rigid scene.

For example, the motion of a sensor in a two-dimensional (2D) plane or the motion of a sensor in a three-dimensional (3D) space. The sensor may be the ground data collecting unit 13, such that the ego-motion calculation unit 1411 may calculate the ego-motion of the ground data collecting unit 13.

The ego-motion calculation unit 1411 may measure the ego-motion of the ground data collecting unit 13 using visual odometry. In visual odometry, the ego-motion of the sensor, such as the camera, is obtained using a moving sensor, for example, a series of a plurality of visible ray images or infrared images collected by the ground data collecting unit 13.

Figure 5:
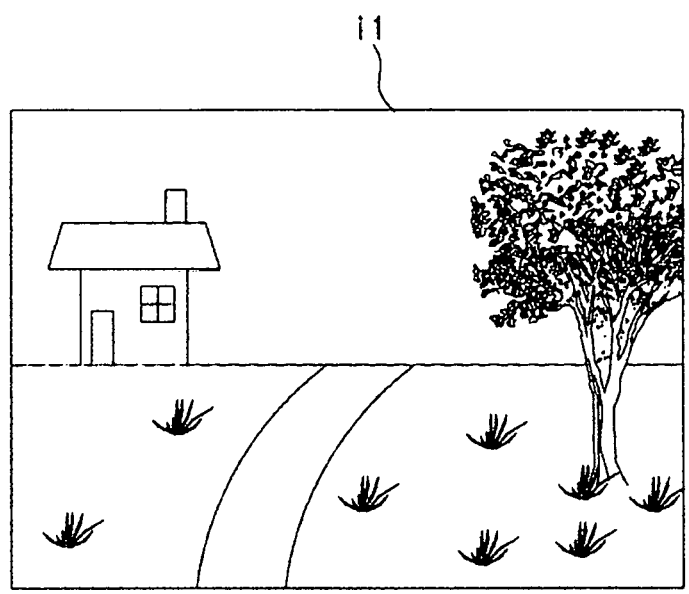
FIGS. 5 through 7 illustrate visual odometry.
Figure 6:
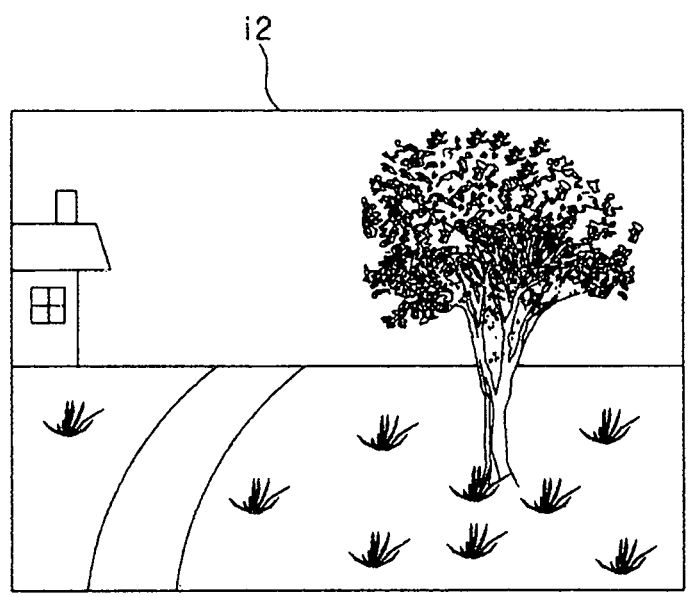
Figure 7:
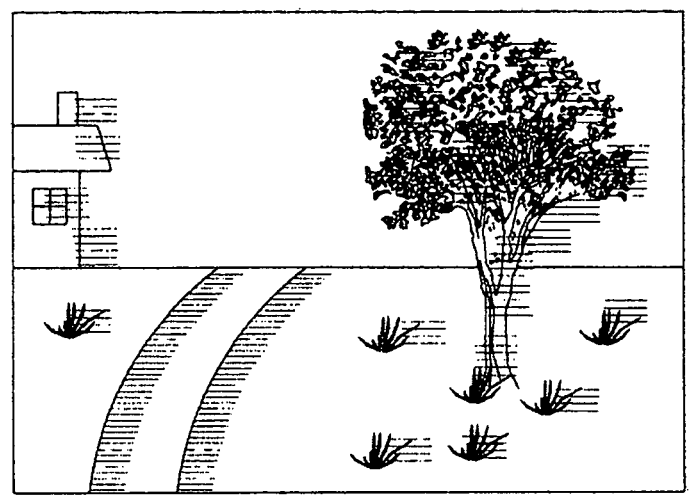

FIGS. 5 through 7 illustrate visual odometry. FIGS. 5 through 7 illustrate a visible ray image as an example of an image. However, in the case of an infrared image, a vector of a motion can be calculated as will be described later.

As illustrated in FIG. 5, the ground data collecting unit 13 may obtain a first image i1 at a first time t by capturing an image of a nearby subject at a particular time t.

As illustrated in FIG. 6, the ground data collecting unit 13 may capture a second image i2 of the nearby subject at a second time (t+Δt) after a desired (or, alternatively, a predetermined) time Δt elapses.

If the ground data collecting unit 13 is moving, a position and a shape of the subject marked on the first image i1 obtained at the first time t and a position and a shape of the subject marked on the second image i2 obtained at the second time (t+Δt) may be different from each other, as illustrated in FIGS. 5 and 6. The ego-motion calculation unit 1411 can estimate and measure the movement of the ground data collecting unit 13 using a difference between two images i1 and i2.

For example, the ego-motion calculation unit 1411 may detect feature points from each of the two images i1 and i2, and calculate motion vectors by measuring a difference between the feature points, for example, a change in the sizes or positions of the feature points. As a result, a plurality of motion vectors corresponding to a plurality of feature points can be obtained, as illustrated in FIG. 7. The ego-motion calculation unit 1411 may calculate and obtain the plurality of motion vectors, thereby calculating the ego-motion of the ground data collecting unit 13.

Figure 8:
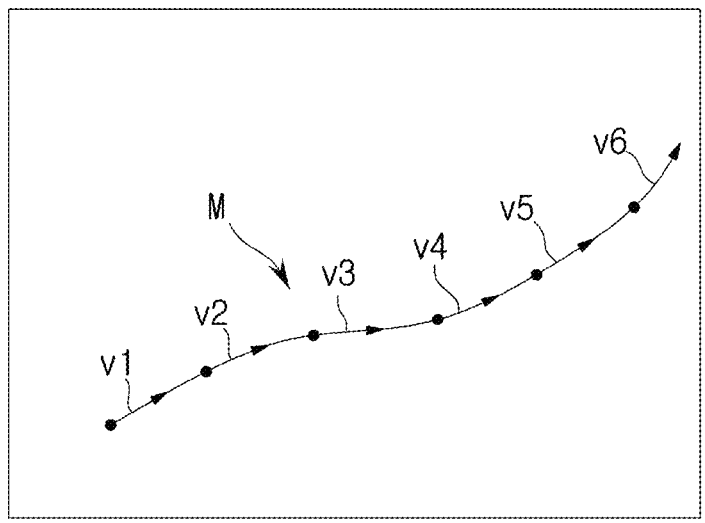
FIG. 8 illustrates an ego-motion in accordance with some example embodiments.

FIG. 8 illustrates an ego-motion in accordance with some example embodiments.

Referring to FIG. 8, if the ground data collecting unit 13 is continuously moved, the ego-motion calculation unit 1411 may calculate the ego-motion continuously. The ego-motion calculation unit 1411 may calculate the ego-motion at desired (or, alternatively, at predetermined) periods. If the ego-motion is calculated for multiple periods, a plurality of motion vectors v1 through v6 can be obtained, as illustrated in FIG. 8. The ego-motion calculation unit 1411 may obtain the ego-motion of the ground data collecting unit 13 by combining the obtained plurality of motion vectors v1 through v6 with each other.

A period in which the ego-motion is calculated may be determined by the designer or wearer. For example, the motion vectors v1 through v6 illustrated in FIG. 8 may be obtained in a period of one second or less or in a period of sixty (60) seconds. Also, the period in which the ego-motion is calculated need not be constant. For example, the ego-motion calculation unit 1411 may calculate the ego-motion in a relatively short period when the walking speed of the wearer of the walk-assistive robot 1 is high and may calculate the ego-motion in a relatively long period when the walking speed of the wearer of the walk-assistive robot 1 is low.

Generating Ground Information

Referring back to FIG. 4, the ground information creating unit 1412 of the controller 14 may generate ground information using the ground data collected by the ground data collecting unit 13. The ground information creating unit 1412 may create ground information by combining the obtained ground data. The created ground information may include a map regarding the ground. In some example embodiments, the ground information creating unit 1412 may create a 3d map regarding the ground. Also, the map regarding the ground may include a map regarding forward, sideward and rearward directions with respect to the walking direction. The ground information creating unit 1412 may create the ground information using the ego-motion obtained by the ego-motion calculation unit 1411.

FIGS. 9 through 13 illustrate a method of creating a map in a walking direction that is an example of ground information in accordance with an example embodiment.

Figure 9:
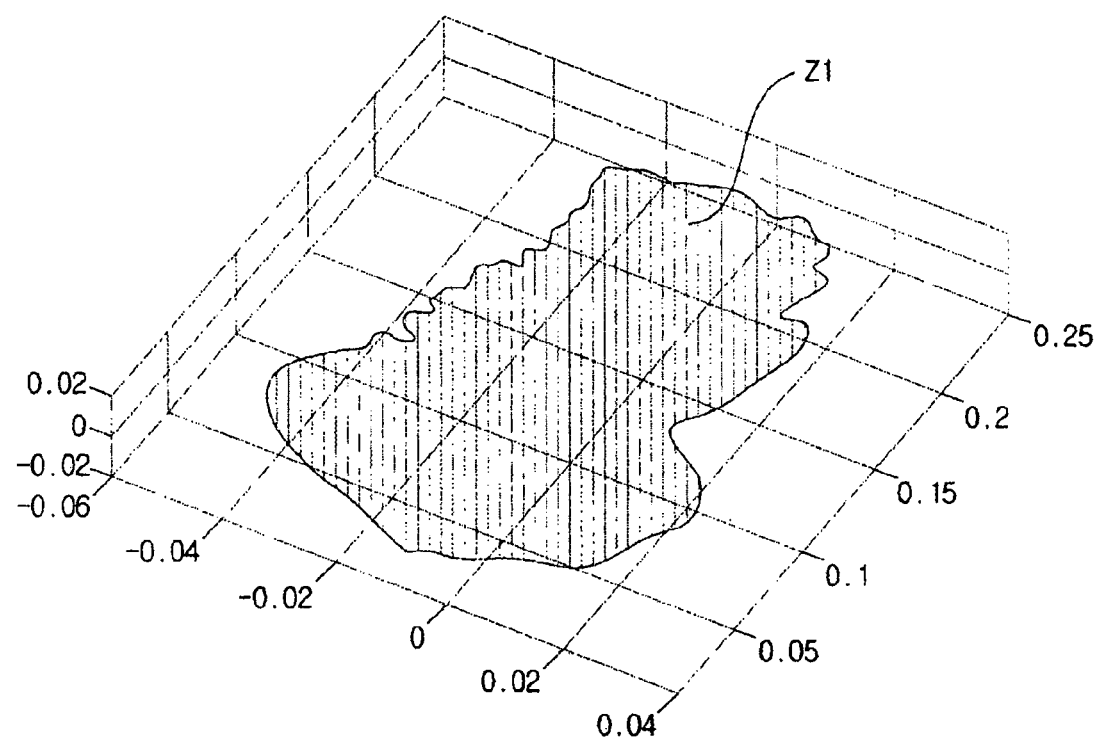
FIGS. 9 through 14 illustrate a method of creating ground information in the form of a map in a walking direction in accordance with some example embodiments.

Referring to FIG. 9, the ground data collecting unit 13 may collect ground data Z1 within a desired (or, alternatively, a predetermined) range of the walk-assistive robot 1 at the first time t, as described above. The ground data Z1 within the range may be 3D data, as illustrated in FIG. 9.

Figure 10:
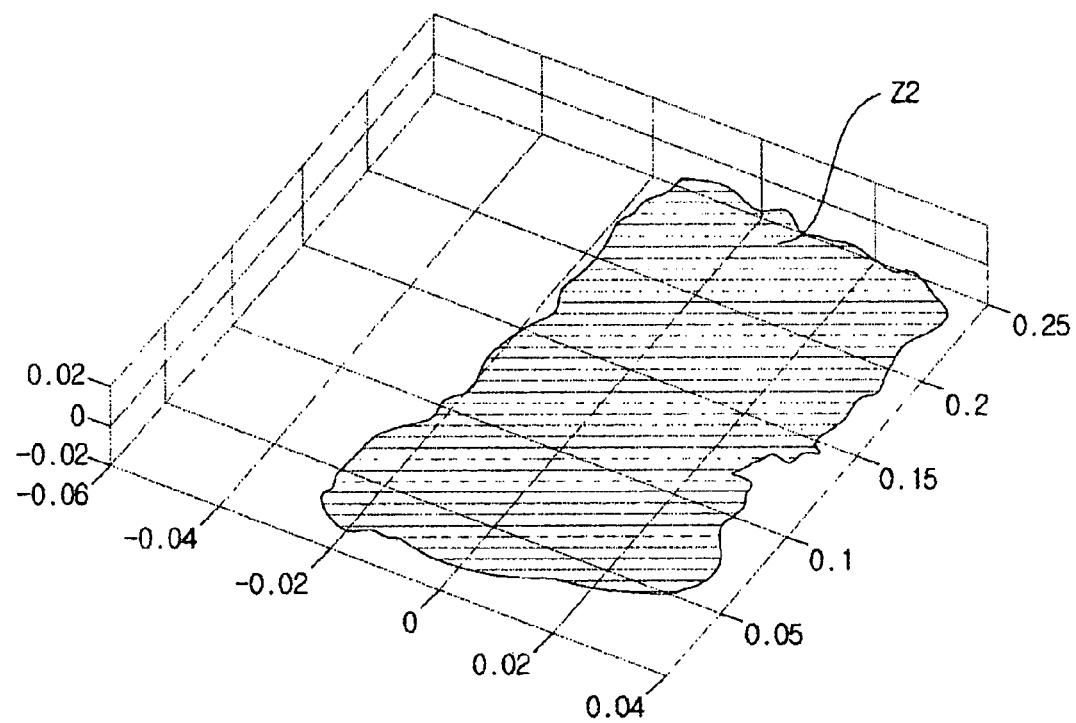

Referring to FIG. 10, if the wearer moves, the ground data collecting unit 13 may collect ground data Z2 within a new range at a second time (t+Δt), after a desired (or, alternatively, a predetermined) time Δt elapses from the first time t.

Figure 11:
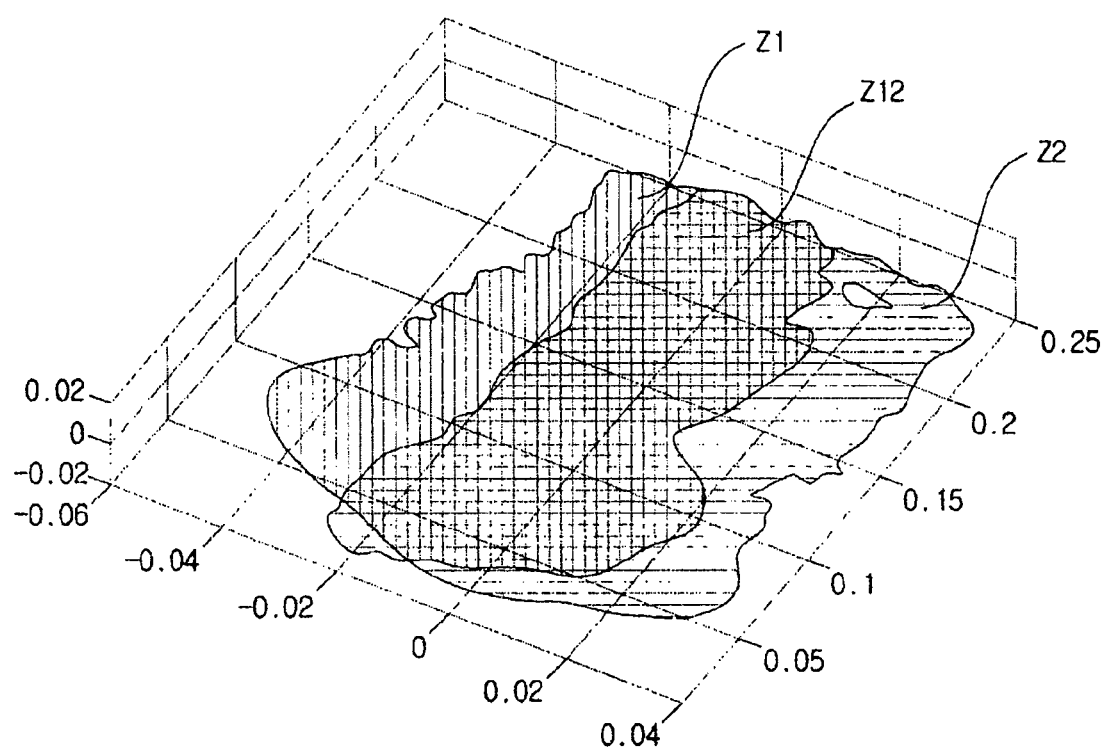

Referring to FIG. 11, the ground data Z1 collected at the first time t and the ground data Z2 collected at the second time (t+Δt) may overlap each other in a desired (or, alternatively, a predetermined) region Z12.

Figure 12:
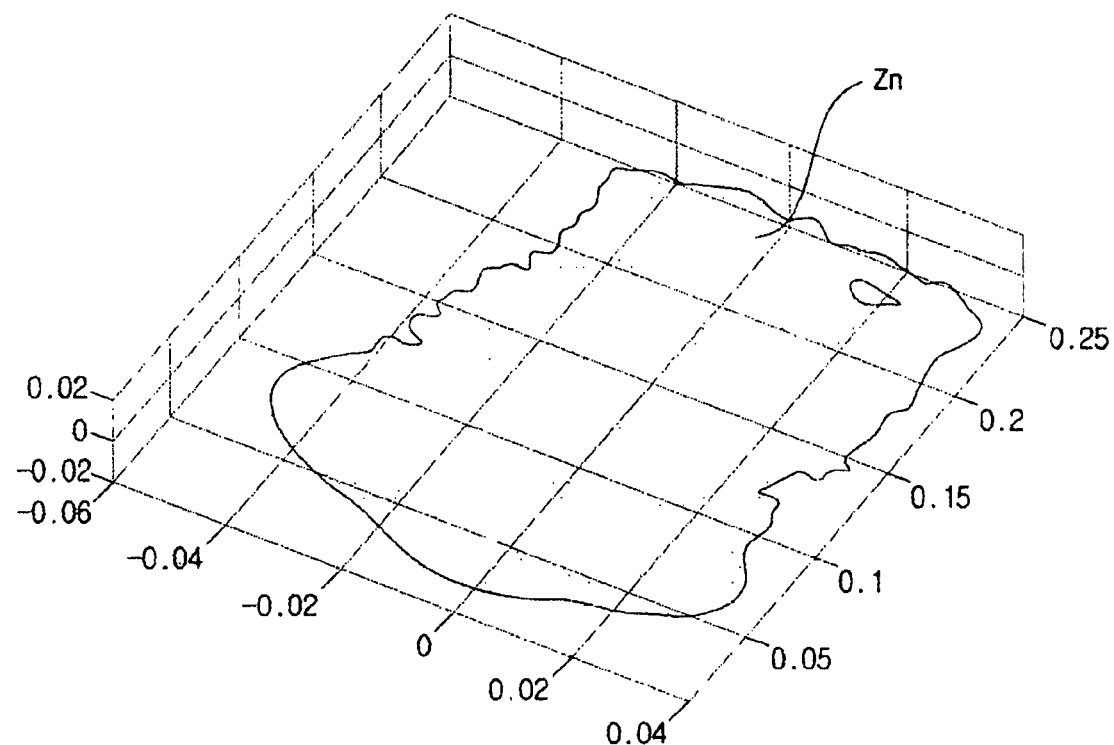

Referring to FIG. 12, the ground information creating unit 1412 may synthesize the ground data Z1 collected at the first time t and the ground data Z2 collected at the second time (t+Δt) using the overlapping portion Z12 to generate synthesized ground data Zn. The synthesized ground data Zn may be a map regarding the ground within a desired (or, alternatively, a predetermined) range.

In some example embodiments, in order to synthesize the ground data Z1 collected at the first time t and the ground data Z2 collected at the second time (t+Δt), the ground information creating unit 1412 may use an iterative closest point (ICP) algorithm. The ground information creating unit 1412 may use the ICP algorithm to minimize a difference between a plurality of clouds of point. For example, using the ICP algorithm, the ground information creating unit 1412 may obtain transformation coefficients between a plurality of points of the plurality of clouds, and obtain the relationship between the plurality of clouds of point.

In more detail, according to the ICP algorithm, first, the ground information creating unit 1412 may select at least one point within one cloud of points selected from among the plurality of clouds of point, and detect at least one point from the other clouds of point that is closest to the selected at least one point. Subsequently, the ground information creating unit 1412 may estimate a transformation coefficient between the point selected within the one cloud of point and the point detected from the other clouds of point. In this case, the transformation coefficient may be estimated using a desired (or alternatively, a predetermined) transformation function, for example, a mean square cost function. Points are transformed using the obtained transformation coefficient so as to obtain newly transformed clouds of point, and the ground information creating unit 1412 repeatedly performs the above-described on a plurality of points within re-transformed clouds of point or a plurality of points within the transformed clouds of point or original clouds of point so that the relationship between the plurality of clouds of point can be obtained.

According to the ICP algorithm, the ground information creating unit 1412 can calculate transformation functions relating to a size change, rotation, and movement for matching the plurality of clouds of point. Since the ICP algorithm can be performed in real-time, the ground information creating unit 1412 can rapidly create the ground information.

In some example embodiments, the ground information creating unit 1412 may cause the ICP algorithm to be performed using an ego-motion value calculated by the ego-motion calculation unit 1411 as an initial value.

In some example embodiments, as illustrated in FIGS. 9 through 12, the ground information creating unit 1412 may create the ground information by combining the plurality of ground data. For example, the ground information creating unit 1412 may create the ground information using the ground data Z1 and Z2 at two times t and t+Δt, as illustrated in FIGS. 9 through 12.

Figure 13:
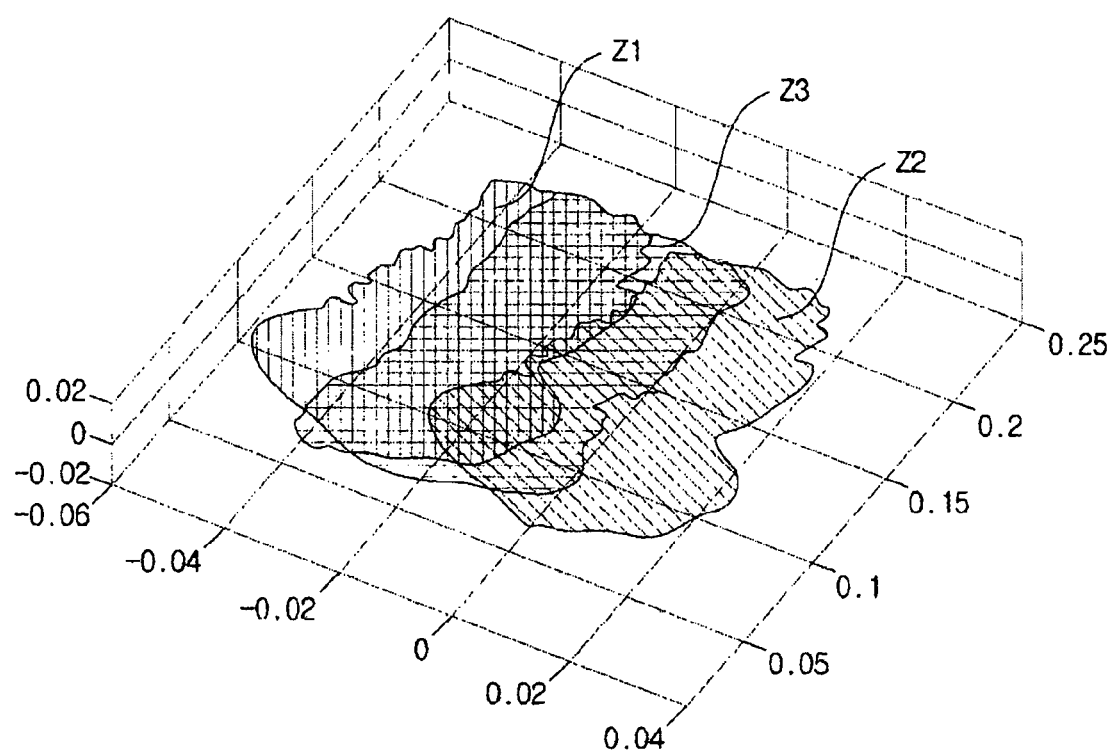

In other example embodiments, as illustrated in FIG. 13, the ground information creating unit 1412 may create the ground information using the ground data Z1 through Z3 at three or more times. When the ground information is created using the ground data Z1 through Z3 at three or more times, the ground information may be created and obtained using various methods. In some example embodiments, first, after the ground data Z1 and Z2 are combined, the ground information creating unit 1412 combines the combined ground information and other ground data Z3 with each other, thereby obtaining final ground information. In other example embodiments, the ground information creating unit 1412 simultaneously combines ground data representing three or more different times, thereby obtaining final ground information.

The ICP algorithm may also be used to combine ground data of three or more times.

Figure 14:
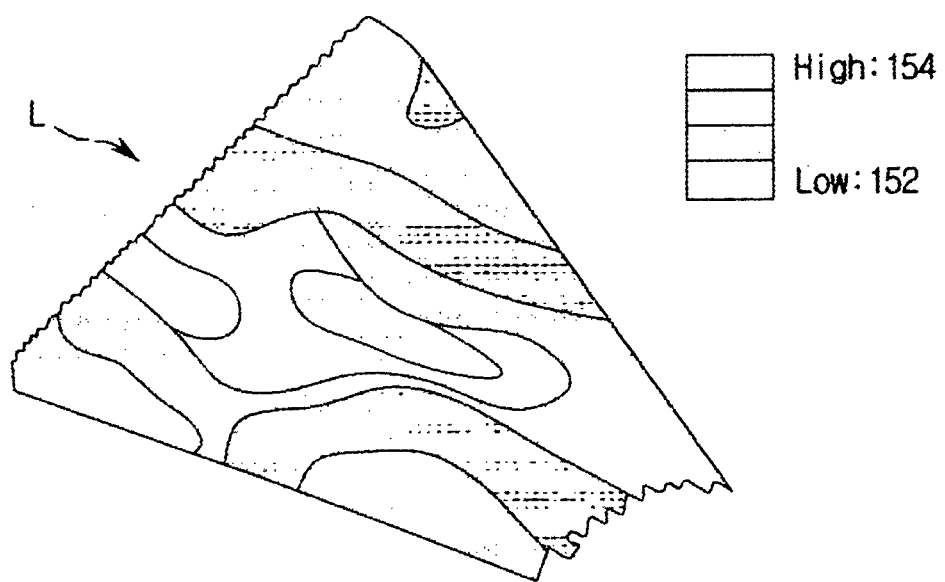

FIG. 14 illustrates an example of ground information in the form of a map regarding the ground located forward in the walking direction.

Referring to FIG. 14, in FIG. 14, for convenience of explanation, an example of the ground information will be described using the map regarding the ground located forward in the walking direction of the wearer. However, a map regarding the ground located sideward or rearward from the walking direction may also be used as an example of the ground information.

The ground information creating unit 1412 may create ground information regarding the wearer's walking direction. For example, the ground information creating unit 1412 may create a map L regarding the ground illustrated in FIG. 14, by combining the plurality of pieces of ground data, as described above with reference to FIGS. 9-13.

The created ground information L may include information regarding a height of all or a part of ground within a desired (or, alternatively, a predetermined) range. In detail, referring to FIG. 14, brighter portions of the ground information L represent higher regions, and darker portions of the ground information L represent lower regions. In other words, the bright portions of the ground information L may be portions that protrude from the ground, and the dark portions of the ground information L may be portions that are recessed in the ground.

The created ground information may be transmitted to a ground shape determining unit 1413. The ground information created according to some example embodiment may be temporarily stored in a storage space, for example, a buffer memory device of the CPU before the ground information is transmitted to the ground shape determining unit 1413. In other example embodiments, the created ground information may also be permanently stored in a separate storage device.

Because a shape of the ground in the walking direction may continuously change according to progression of the wearer walking, the ground information creating unit 1412 may create the ground information for each period. Therefore, the ground information creating unit 1412 may create ground information whenever the ground data is collected. However, the ground information creating unit 1412 need not create ground information whenever the ground data is collected. For example, partial ground data may be discarded without being used when collecting ground information. The ground information created by the ground information creating unit 1412 may be discarded in each period.

Figure 15:
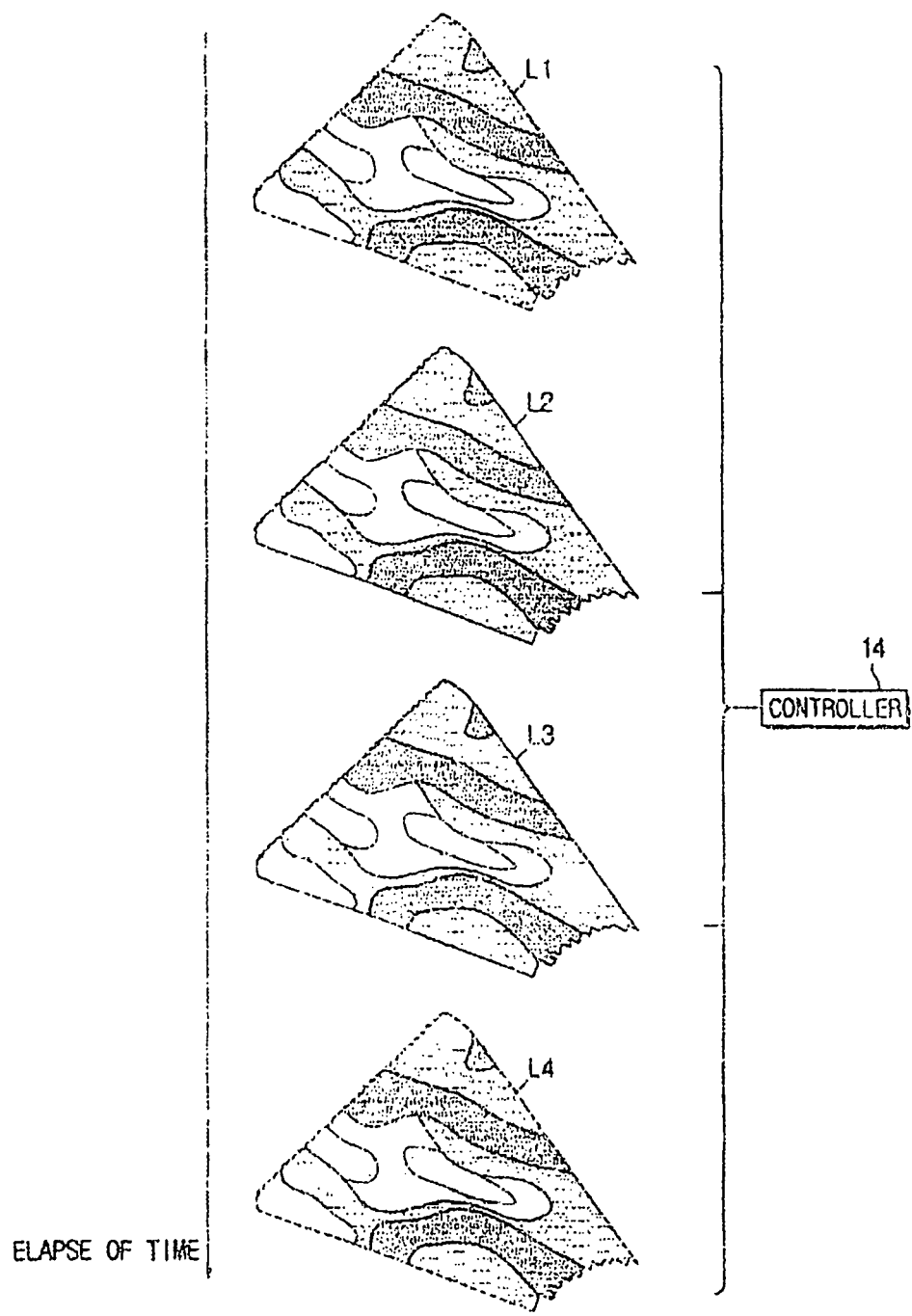
FIG. 15 illustrates a method of managing the map in the walking direction in accordance with some example embodiments.

FIG. 15 illustrates a method of managing ground information in accordance with an example embodiment.

Referring to FIG. 15, the ground information creating unit 1412 of the controller 14 may first create first ground information L1 and, thereafter, may create new, second ground information L2 after a desired (or, alternatively, a predetermined) amount of time elapses. Likewise, if a desired (or, alternatively, a predetermined) amount of time elapses again, the ground information creating unit 1412 of the controller 14 may create new third ground information L3. Further, if a desired (or, alternatively, a predetermined) amount of time elapses again, the ground information creating unit 1412 of the controller 14 may create new fourth ground information L4.

As the wearer continues to move, the created ground information may become unnecessary if a desired (or, alternatively, a predetermined) amount of time elapses and/or the wearer moves a certain distance. For example, the first ground information L1 may be information regarding the ground that the wearer has already traversed. Thus, the first ground information L1 may be ground information that is not necessary any more. In this case, the controller 14 may discard the first ground information L1. For example, the controller 14 may discard the first ground information L1 by deleting the first ground information L1 from the storage device, such as the buffer memory device.

The controller 14 may control the walk-assistive robot 1 by creating control signals for controlling the walk-operating units 20 through 40 based on the created ground information.

Determining a Type of Ground

Referring back to FIG. 4, in some example embodiment, the controller 14 may determine control patterns of the walk-assistive robot 1 based on the created ground information and may generate control signals for controlling the walk-assistive robot 1 according to the determined control patterns.

In detail, the controller 14 may execute computer readable instructions that configure the controller 14 as the ground shape determining unit 1413 and the control pattern determining unit 1414, as illustrated in FIG. 4. The ground shape determining unit 1413 may determine the shape of the ground using the created ground information.

Figure 16:
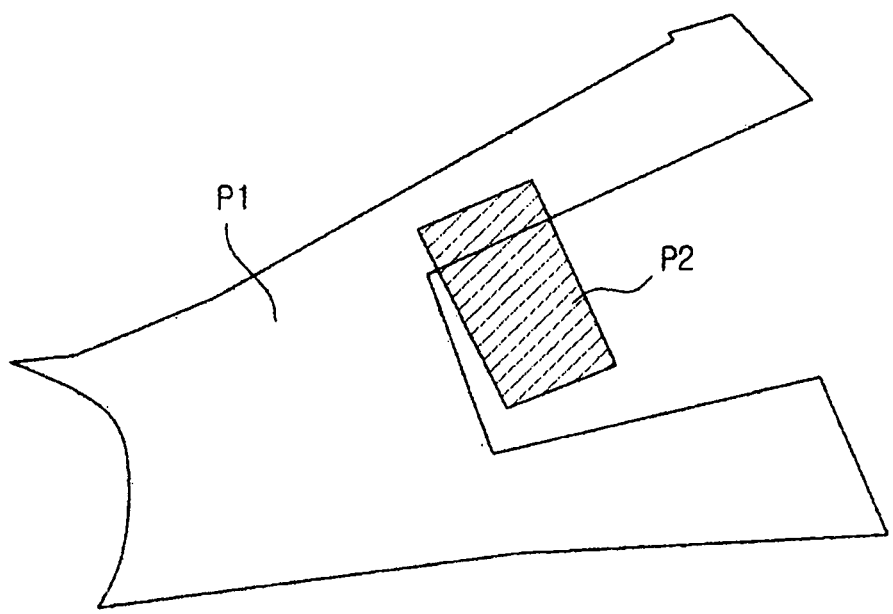
FIG. 16 is a view for explaining reference ground and comparison ground.

FIG. 16 is a view for explaining reference ground and comparison ground.

Referring to FIG. 16, in some example embodiments, the ground shape determining unit 1413 may extract information on a reference ground (or terrain) P1 and comparison ground (or terrain) P2 from the ground information L and may determine a type of the ground located forward in the walking direction using the reference ground P1 and the comparison ground P2, as illustrated in FIG. 16. For example, the ground shape determining unit 1413 may determine whether the ground (or terrain) located forward in the walking direction of the wearer is flatland ground, stair ground, uphill ground, or downhill ground.

The reference ground P1 is a region that is a reference for comparison of the ground among the ground information L. When the ground information is information regarding the ground in the walking direction, the reference ground P1 may be partial ground among ground in the walking direction.

The ground shape determining unit 1413 may select a desired (or, alternatively, a predetermined) region from the ground information L and may determine the selected region as the reference ground P1. In some example embodiments, the ground shape determining unit 1413 may select a region in a widest range from the ground information L as the reference ground P1.

The ground shape determining unit 1413 may classify the ground information L according to direction and height and may determine one among a plurality of regions classified as the reference ground P1. Thus, the reference ground P1 may have a value of only one direction and height. If ground information L1 through L4 is created a plurality of times, the ground shape determining unit 1413 may select reference ground extracted from the ground information L1 that has already been used as the reference ground P1 of the ground information L2 for determining a new ground shape. In other words, the reference ground P1 that is newly extracted from the new ground information L2 may be the same as reference ground of the ground information extracted from the ground information L that has already been used.

The comparison ground P2 is a region that is compared with the reference ground P1 for determining the shape of the ground among the ground information L. If the ground information is information regarding the ground in the walking direction, the comparison ground P2 may be partial ground that is different from the reference ground P1 among the ground in the walking direction.

The ground shape determining unit 1413 may select all portions or a portion of other regions that do not correspond to the reference ground P1 as the comparison ground P2. In this case, all ground that is not selected as the reference ground P1 may be determined by the ground shape determining unit 1413 as the comparison ground P2.

In some example embodiments, the ground shape determining unit 1413 may determine only one particular region among one piece of ground information as the comparison ground P2, as illustrated in FIG. 16. In other example embodiments, the ground shape determining unit 1413 may also determine a plurality of regions as the comparison ground P2

Figure 17:
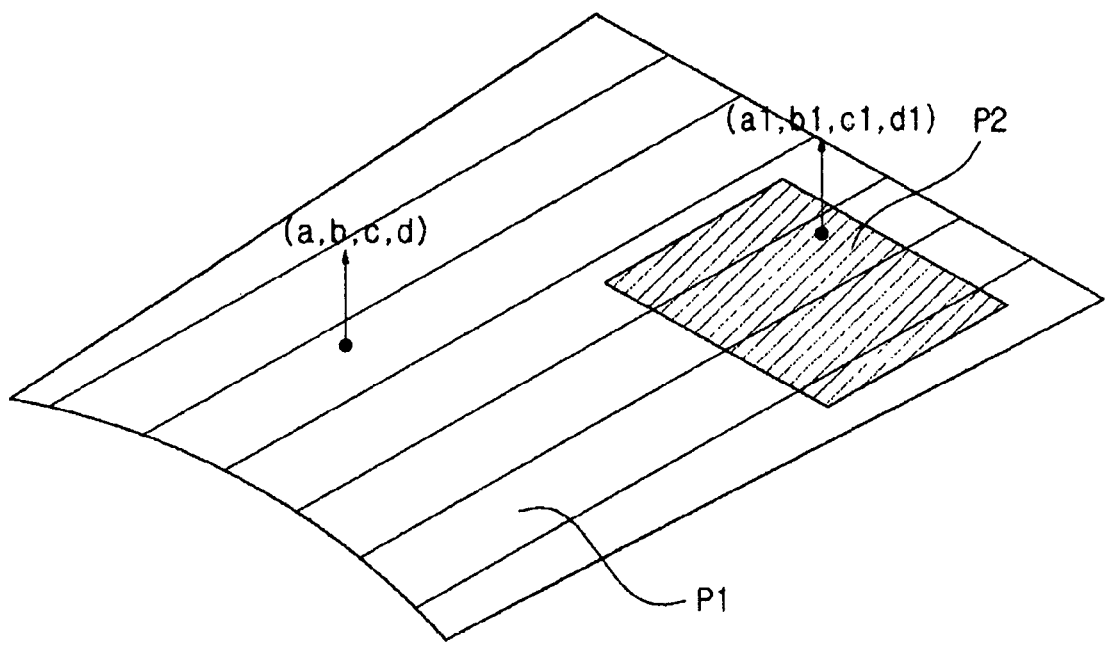
FIG. 17 is another view for explaining reference ground and comparison ground.

FIG. 17 is another view for explaining reference ground and comparison ground.

Referring to FIG. 17, the ground shape determining unit 1413 may determine at least one of the reference ground P1 and the comparison ground P2 using a RANdom SAmple Consensus (RANSAC) algorithm.

The ground shape determining unit 1413 may use the RANSAC algorithm to estimate parameters of a mathematical model from a plurality of data sets which contain outliers through iterative processing. The estimated mathematical model may be a one-dimensional equation, a two-dimensional equation, or a higher dimensional equation. Likewise, the estimated mathematical model may be an exponential equation or a log equation.

In some example embodiments, the ground shape determining unit 1413 may obtain a plurality of equations from the plurality of data sets contained in the created ground information using the RANSAC algorithm. The plurality of equations obtained according to the RANSAC algorithm may be a plurality of regions having different heights or directions. The ground shape determining unit 1413 may determine one among a plurality of different regions expressed by the obtained plurality of equations as the reference ground P1 and may determine the other regions as the comparison ground P2. In this case, the reference ground P1 may be expressed as the following Equation 1.

$$ax+by+cz+d=0 \quad \text{[Equation 1]}$$

In Equation 1, a, b, and c are directions of the reference ground P1. d in Equation 1 is a value that may be determined by a position, for example, a height of the reference ground P1. Coefficients of Equation 1 may be expressed in the form of a vector, as illustrated in the reference ground P1 of FIG. 17, as such, Equation 1 may be rewritten in vector form as the following Equation 2.

$$\vec{v}=(a,b,c,d) \quad \text{[Equation 2]}$$

Likewise, the comparison ground P2 may be expressed as the following Equation 3.

$$a_1 x+b_1 y+c_1 z+d_1=0 \quad \text{[Equation 3]}$$

In Equation 3, $a_1$, $b_1$, and $c_1$ are directions of the comparison ground P2, and $d_1$ is a value that may be determined according to a position, for example, a height, of the comparison ground P2. As described above, coefficients of Equation 3 may be expressed in the form of a vector, as illustrated in the comparison ground P2 of FIG. 17, as such Equation 3 may be rewritten in vector form as the following Equation 4.

$$\vec{v_1}=(a_1,b_1,c_1,d_1) \quad \text{[Equation 4]}$$

In other example embodiments, the ground shape determining unit 1413 may determine the reference ground P1 and the comparison ground P2, may obtain an equation for expressing the reference ground P1 among the plurality of data sets contained in the reference ground P1 among the ground information created using the RANSAC algorithm, and may obtain an equation for expressing the comparison ground P2 among the plurality of data sets contained in the comparison ground P2 among the ground information created in the same manner. The equation for expressing the reference ground P1 and the equation for expressing the comparison ground P2 may be written as the above Equations 1 and 3, respectively. Likewise, in vector form, the equation for expressing the reference ground P1 and the equation for expressing the comparison ground P2 may be written as the above Equations 2 and 4, respectively.

The ground shape determining unit 1413 may determine a shape of the ground using the determined reference ground P1 and comparison ground P2. The ground shape determining unit 1413 may refer to a ground database 1420 to determine the shape of the ground. In detail, the ground shape determining unit 1413 may obtain information regarding the reference ground P1 and the comparison ground P2 and then may determine the shape of the ground by searching the ground database 1420 for a portion corresponding to the obtained information.

Figure 18:
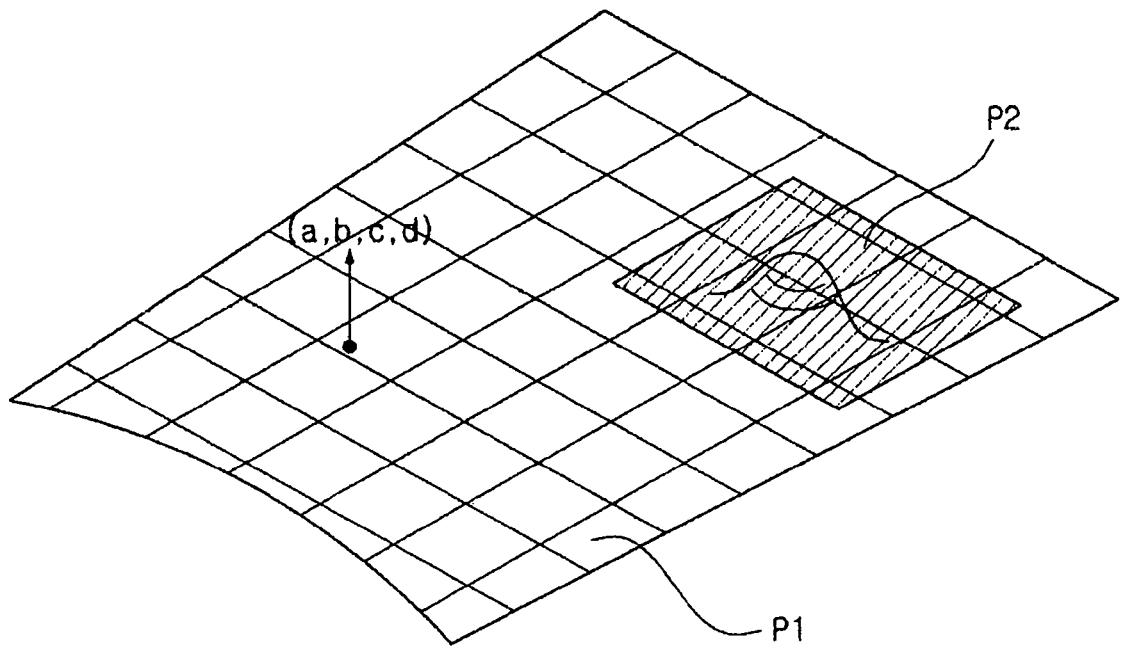
FIGS. 18 through 20 illustrate a method of determining at least one ground shape according to the reference ground and the comparison ground in accordance with some example embodiments.

FIG. 18 is a view for explaining an example of ground determined according to the reference ground and the comparison ground.

Referring to FIG. 18, in some example embodiments, the ground shape determining unit 1413 may compare the size of the reference ground P1 with the size of the comparison ground P2 and may determine the shape of the ground according to the result of comparison. For example, if the ground shape determining unit 1413 determines that the width of the comparison ground P2 is smaller than the width of the reference ground P1 by a desired (or, alternatively, a predetermined) value or ratio, the ground shape determining unit 1413 may determine the comparison ground P2 as uneven. The value or ratio may be stored in the ground database 1420.

In other example embodiments, the ground shape determining unit 1413 may calculate an absolute width of the comparison ground P2 and may determine the comparison ground P2 as an obstacle, for example, an uneven terrain, if the absolute width of the comparison ground P2 is smaller than the value. If it is determined that the comparison ground P2 is an obstacle, for example, uneven terrain, the ground shape determining unit 1413 may extract information regarding the position or size of the comparison ground P2 from the ground information and may reflect the extracted information regarding the position or size of the comparison ground P2 in controlling the walk-assistive robot 1.

In some example embodiments, the ground shape determining unit 1413 may determine the shape of the ground using an equation or a vector value of the reference ground P1 or an equation or a vector value of the comparison ground P2, for example, the ground shape determining unit 1413 may determine the shape of the ground using one or more of equations 1 to 4.

Figure 19:
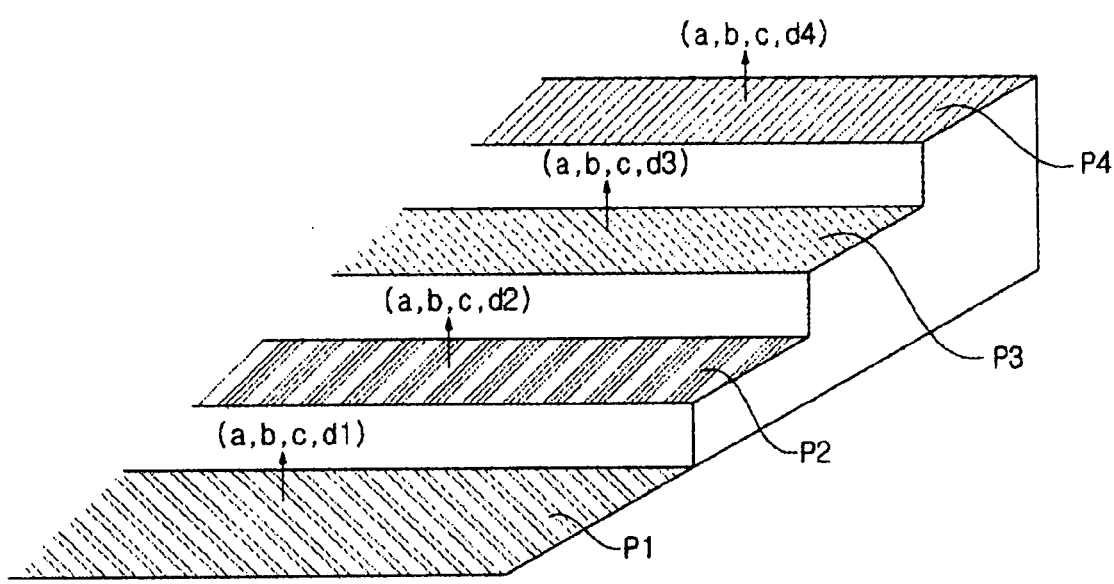

FIG. 19 is a view for explaining another example of ground determined according to the reference ground and the comparison ground.

Referring to FIG. 19, if one region of reference ground P1 and a plurality of regions of comparison ground P2 through P4 are determined, as illustrated in FIG. 19, the ground shape determining unit 1413 may compare directions and heights of the reference ground P1 and the comparison ground P2 through P4. If directions a, b, and c of the reference ground P1 and the comparison ground P2 through P4 are the same or similar, as illustrated in FIG. 19 and only values d are drastically different from each other, the ground shape determining unit 1413 may determine the shape of the ground as stairs.

Referring to FIG. 19, if directions a, b, and c of the reference ground P1 and the plurality of comparison grounds P2 through P4 are the same, the reference ground P1 and the plurality of comparison grounds P2 through P4 are substantially parallel to each other. However, since values d that may be determined according to the positions of the reference ground P1 and the plurality of grounds P2 through P4 are different from each other, positions between the reference ground P1 and the plurality of comparison grounds P2 through P4, i.e., heights therebetween, may be different from each other. Thus, the ground shape determining unit 1413 may determine that the ground information indicates that the ground has a plurality of regions that are substantially parallel and have different heights, and the shape of the ground corresponding to the ground information is stair-shaped. Thus, the ground shape determining unit 1413 may determine the shape of the ground as stairs.

FIG. 19 illustrates only a case of uphill stairs, however, example embodiments are not limited thereto. For example, in a case of downhill stairs, the ground shape determining unit 1413 may determine the shape of the ground as stairs. In this case, the values d that may be determined according to the positions of the ground may be different from those of the uphill stairs. Thus, the ground shape determining unit 1413 may determine whether stairs in the walking direction are uphill stairs or downhill stairs according to the values d that may be determined according to the positions of the ground. For example, depending on whether the values of d are increasing or decreasing between each of the plurality of grounds P2 through P4.

Figure 20:
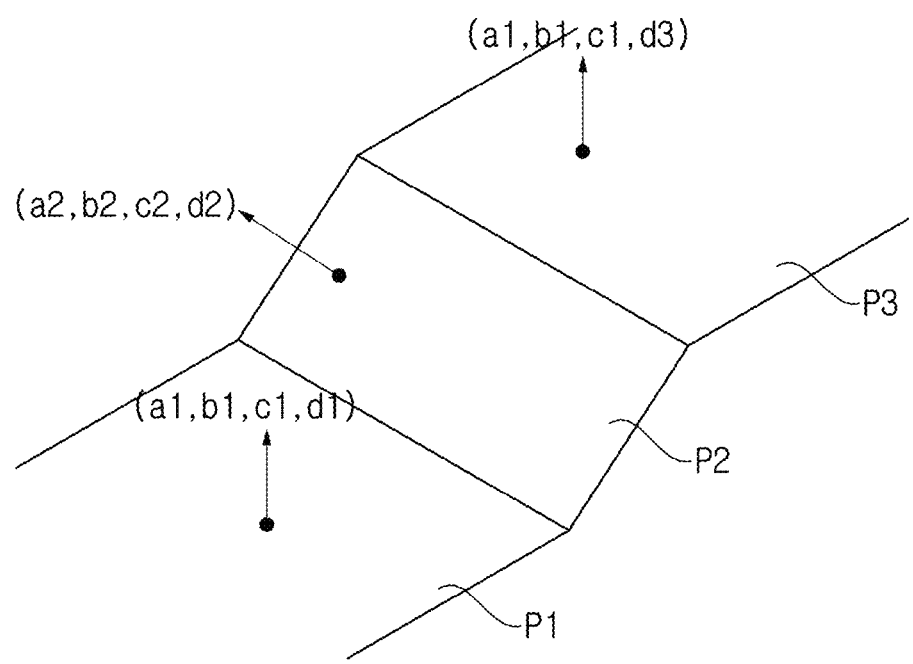

FIG. 20 is a view illustrating another example of ground that is determined according to the reference ground and the comparison ground.

Referring to FIG. 20, when one region of reference ground P1 and a plurality of regions of comparison ground P2 and P3 are determined, the ground shape determining unit 1413 may compare directions and heights of the reference ground P1 and the comparison ground P2 and P3, as described above. If directions a2, b2, and c2 of the comparison ground P2 are different from directions a1, b1, and c1 of the reference ground P1, as illustrated in FIG. 20, the ground shape determining unit 1413 may determine the shape of the ground as an uphill inclination or a downhill inclination.

If directions a1, b1, and c1 of the reference ground P1 and directions a2, b2, and c2 of the comparison ground P2 are different from each other, the reference ground P1 and the comparison ground P2 may not be parallel to each other. Thus, an angle between the reference ground P1 and the comparison ground P2 may have a non-zero value. In this way, if the angle between the reference ground P1 and the comparison ground P2 is not zero, inclinations of the ground are different from each other, and thus the ground shape determining unit 1413 may determine the shape of the ground as an uphill inclination or a downhill inclination. If the reference ground P1 is a flatland, the comparison ground P2 may be determined as an uphill inclination or a downhill inclination. If the reference ground P1 is not a flatland but an uphill inclination or a downhill inclination, the comparison ground P2 may be determined as the flatland, the uphill inclination, or the downhill inclination. If the reference ground P1 is the uphill inclination or the downhill inclination, a type of the comparison ground P2 may also be determined by the angle between the reference ground P1 and the comparison ground P2. The angle between the reference ground P1 and the comparison ground P2 may be calculated using various formulas for obtaining an angle between a plurality of vectors.

In this case, it may be determined whether the comparison ground P2 is the uphill inclination or the downhill inclination based on a value d of the comparison ground P2 corresponding to the inclination ground. Alternatively, it may also be determined whether one comparison ground P2 is the uphill inclination or the downhill inclination based on a position of the reference ground P and a position of another comparison ground P3, i.e., a height of the comparison ground P3. If the position of another comparison ground P3 is higher than the position of the reference ground P1, one comparison ground P2 may be determined as the uphill inclination. In contrast, if the position of another comparison ground P3 is lower than the position of the reference ground P1, one comparison ground P2 may be determined as the downhill inclination.

Meanwhile, when directions a1, b1, and c1 of another comparison ground P3 are the same as a1, b1, and c1 of the reference ground P1 and only the value d is different, the reference ground P1 and the other comparison ground P3 are parallel to each other and have different heights. Thus, the ground shape determining unit 1413 may determine that the uphill or downhill inclination is completed at the other comparison ground P3.

If the ground shape determining unit 1413 determines the shape of the ground, the determined shape of the ground may be transmitted to the control pattern determining unit 1414 of the controller 14

Determining Control Patterns Based on the Type of Ground

Referring back to FIG. 4, the control pattern determining unit 1414 of the controller 14 may determine control patterns of the walk-assistive robot 1 according to the shape of the ground determined by the ground shape determining unit 1413. For example, if there is an obstacle on the ground, as illustrated in FIG. 18, the control pattern determining unit 1414 may determine control patterns of the walk-assistive robot 1 so as to avoid the obstacle on the ground. If the shape of the ground is stairs, as illustrated in FIG. 19, the control pattern determining unit 1414 may determine control patterns of the walk-assistive robot 1 so as to assist the wearer in going up or down stairs. If the shape of the ground is the uphill inclination or the downhill inclination, as illustrated in FIG. 20, the control pattern determining unit 1414 may determine control patterns of the walk-assistive robot 1 so as to assist the wearer in walking along the uphill or downhill inclination.

In some example embodiments, the control pattern determining unit 1414 may determine control patterns of the walk-assistive robot 1 by reading control patterns corresponding to the walking environment from the control pattern database 1421.

Various control patterns for assisting the wearer according to the shape of the ground that is the wearer's walking environment may be stored in the control pattern database 1421. The following Table 1 shows an example of various patterns that may be stored in the control pattern database 1421.

TABLE 1

| Shape of ground | Control pattern |
| --- | --- |
| Flatland | Assist with walking according to a normal walking cycle |
| Obstacle (unevenness) | Assist with walking while avoiding obstacle |
| Downhill inclination | Assist with walking downward |
| Uphill inclination | Assist with walking upward |
| Downhill stairs | Assist with walking downward and simultaneously guide soles toward top surfaces of stairs at bottom end of ground |
| Uphill stairs | Assist with walking upward and simultaneously guide soles toward top surfaces of stairs at top end of ground |

The controller 14 may include a control signal generating unit 1415. If the control pattern determining unit 1414 determines control patterns of the walk-assistive robot 1, the control signal generating unit 1415 may generate control signals according to the determined control patterns and may transmit the generated control signals to at least one of the first driving portions 21a and 21b and the second driving portions 31a and 31b. The walk-operating units 20 through 40 of the walk-assistive robot 1 may be driven to assist the wearer with walking according to the control signals transmitted by the control signal generating unit 1415.

Hereinafter, an example in which the walk-assistive robot 1 is driven according to control signals will be described. The driving example of the walk-assistive robot 1 that will be described below is merely an example, and there may be various driving examples.

When the walk-assistive robot 1 is on a flatland, as shown in Table 1, the walk-assistive robot 1 may be controlled to assist with walking according to a normal walking cycle.

If there is an obstacle on the ground, the first driving portions 21a and 21b worn on legs may be controlled to generate larger rotational force than in the normal walking cycle as the wearer approaches the obstacle. As a result, the wearer may more easily raise his/her thighs higher than in the normal walking so as to avoid the obstacle.

If the ground on which the wearer is walking or will walk has an uphill inclination, the first driving portions 21a and 21b may be rotated in a desired (or, alternatively, a predetermined) direction with a relatively larger rotational force than in the normal walking according to a gradient so that the user can more easily raise his/her thighs. Subsequently, the first driving portions 21a and 21b may be rotated in an opposite direction shorter than in normal walking and may cause the user's foot to contact the ground in a higher position than the ground which the user's foot contacts before the user raises his/her thigh.

While the wearer is walking up stairs or before the wearer goes up stairs, the first driving portions 21a and 21b may be rotated in a desired (or, alternatively, a predetermined) direction with relatively larger rotational forces than in the normal walking so that the user can more easily raise his/her thighs. Subsequently, the first driving portions 21a and 21b may be rotated in the opposite direction shorter than in the normal walking, and the second driving portions 31a and 31b may be rotated at a desired (or, alternatively, a predetermined) angle so that the wearer's feet can be mounted on the top surface of stairs and the second driving portions 31a and 31b can assist the user in more easily going up stairs.

Referring back to FIG. 4, the body 10 of the walk-assistive robot 1 may further include a battery 15 for supplying power to the ground data collecting unit 13 and the controller 14 described above as needed. The battery 15 may be a primary battery or a secondary battery. In some example embodiments, the body 10 may further include a separate generator, instead of or in addition to the battery 15.

Hereinafter, a walk-assistive robot in accordance with other example embodiments will be described with reference to FIG. 21.

Figure 21:
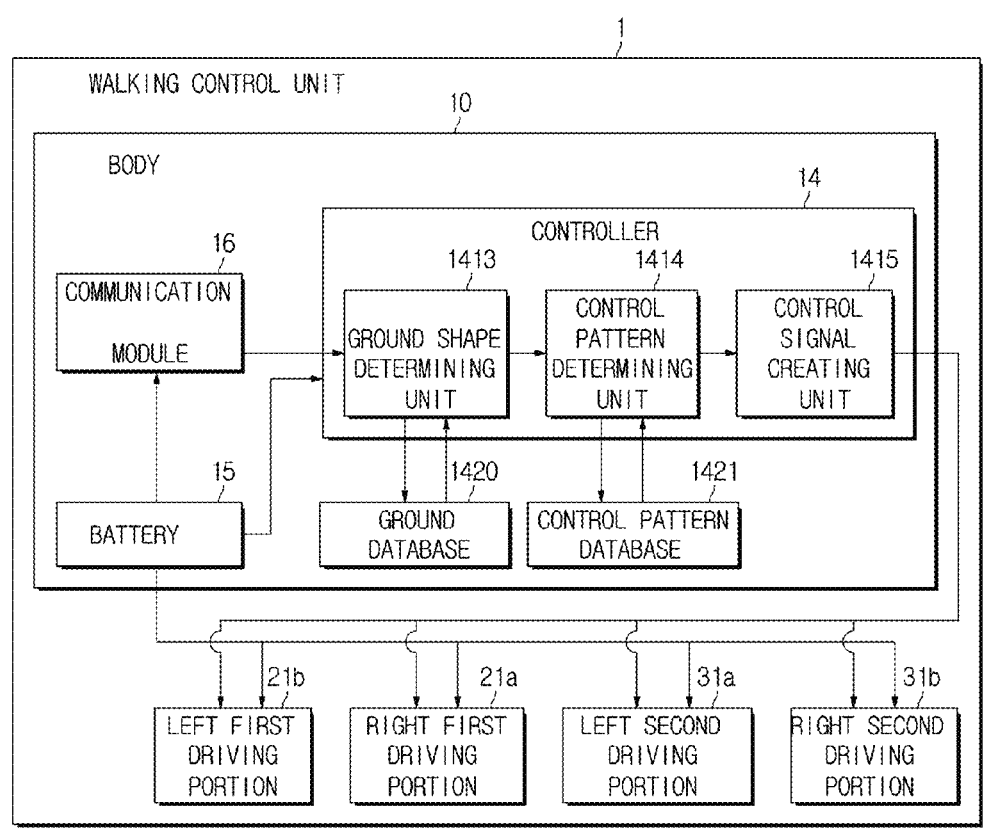
FIG. 21 illustrates a configuration of a walk-assistive robot in accordance with other example embodiments.

Referring to FIG. 21, the walking control unit of the walk-assistive robot 1 may further include a communication module 16. The communication module 16 may transmit data to an external device using a wired or wireless communication network or may receive data from the external device. For example, the communication module 16 may receive ground information from the external device.

In some example embodiments, when the designer or wearer obtains ground information regarding a position, establishes the ground information in the form of a database, the communication module 16 may provide the database to a server device. Thereafter, the communication module 16 of the walk-assistive robot 1 may receive the ground information from the server device.

In some example embodiments, the communication module 16 of the walk-assistive robot 1 of the wearer that moves to a particular region may receive the ground information generated in a walk-assistive robot 1 of another wearer who has already moved to the particular region. In this case, the communication module 16 of the walk-assistive robot 1 of another wearer may transmit the generated ground information to the communication module 16 of the wearer's walk-assistive robot 1.

If the wearer is at a place in which the ground information regarding the ground has already been obtained, the communication module 16 may receive the ground information corresponding to the place at which the wearer obtains the ground information, and may transmit the received ground information to the ground shape determining unit 1413. In this case, when various location systems including a Global Positioning System (GPS) are used, the walk-assistive robot 1 may check whether the wearer is at the place in which the ground information regarding the ground has already been obtained.

As described above, the ground information, for example, the map of the walking direction is created based on the ground data collected by the ground data collecting units 13a and 13b and/or is received through the communication module 16. However, in other example embodiments, the ground information may also be stored in a storage unit of the walk-assistive robot 1. In this case, the ground information may already have been created or obtained before the wearer moves to the region.

Hereinafter, a method of controlling a walk-assistive robot in accordance with example embodiments will be described with reference to FIGS. 22 through 24.

FIG. 22 is a flowchart illustrating a method of controlling a walk-assistive robot in accordance with an example embodiment.

Referring to FIG. 22, the controller 14 may control the walk-assistive robot 1 by obtaining ground information (S100), determining control patterns of the walk-assistive robot 1 based on the obtained ground information (S200), and controlling the walk-assistive robot 1 according to the determined control patterns (S300).

In some example embodiments, the controller 14 may obtain the ground information from the ground data collecting unit 13 (S100). In other example embodiments, the controller 14 may obtain the ground information from the communication module 16 (S100).

FIG. 23 is a flowchart illustrating a method of obtaining ground information in accordance with some example embodiments.

Referring to FIG. 23, the controller 14 may obtain the ground information (S100) by: obtaining a plurality of pieces of ground data (S110) using the ground data collecting unit 13, calculating an ego-motion of the ground data collecting unit 13 (S120), synthesizing the plurality of pieces of ground data (S130), and obtaining the ground information (S140).

The controller 14 may utilize a CPU or a GPU to calculate the ego-motion (S120), synthesize the ground data (S130), and obtain the ground information (S140). For example, the CPU and GPU may be an arithmetic operation logic operation unit, a digital signal processor, a microcomputer, a field programmable array, a programmable logic unit, a microprocessor, a register, a program counter, a command decoder, a control circuit or any other device capable of responding to and executing instructions in a defined manner.

The ground data collecting unit 13 illustrated in FIGS. 1 through 4 may obtain the plurality of pieces of ground data by converting visible rays or infrared rays collected by the ground data collecting unit 13 into electrical signals. The plurality of pieces of ground data may include ground data regarding forward, rearward, and sideward directions with respect to a walking direction of the wearer of the walk-assistive robot 1.

The ego-motion calculating unit 1411 may calculate the ego-motion of the ground data collecting unit 13 using the plurality of pieces of ground data obtained with respect to the walking direction, as illustrated in FIGS. 5 through 8 (S120).

The ground information creating unit 1412 may synthesize (S130) the plurality of pieces of ground data, as illustrated in FIGS. 9 through 13. The ego-motion calculating unit 1411 may calculate the ego-motion in operation S120 before or after synthesizing the plurality of pieces of ground data in operation S130.

The ground information creating unit 1412 may obtain ground information (S140). The ground information may be a map, for example, the map illustrated in FIG. 14. The ground information may be obtained in a desired (or, alternatively, a predetermined) period and ground information that has expired may be removed.

Referring back to FIG. 22, in operation S200, the controller 14 may determine control patterns of the walk-assistive robot 1 based on the obtained ground information. In operation S300, the controller 14 may control the walk-assistive robot 1 according to the determined control patterns.

FIG. 24 is a flowchart illustrating a method of controlling a walk-assistive robot in accordance with other example embodiments.

Referring to FIG. 24, as described above, after the ground information, for example, the map illustrated in FIG. 15, is obtained, the ground shape determining unit 1413 may extract a reference ground from the map (S210). Further, the ground shape determining unit 1413 may extract a comparison ground from the map simultaneously with extracting the reference ground or after the reference ground is extracted (S220).

The reference ground may be a desired (or, alternatively, a predetermined) region that is selected from the map, for example, by the wearer. Alternatively, a region having a widest range of the map may be selected as the reference ground. The comparison ground may be another region that does not correspond to the reference ground from the map. One or several regions may be extracted from the map as comparison ground.

The control pattern determining unit 1414 may determine control patterns using at least one of the reference ground and the comparison ground.

For example, in operation S230, the ground shape determining unit 1413, may compare a width of an area of the comparison ground with a desired (or, alternatively, a predetermined) value. If the area of the comparison ground is smaller than the desired value, in operation S231, the ground shape determining unit 1413 may determine that the comparison ground is an obstacle, for example, uneven ground. Then, the ground shape determining unit 1413 may obtain a position and a size of the comparison ground, and extract information regarding a position of an obstacle, for example, unevenness (S232). Subsequently, the control pattern determining unit 1414 may determine new control patterns for avoiding the obstacle according to the extracted position and size of the comparison ground (S270) and the control signal generating unit 1415 may generate control signals to control the walk-assistive robot 1 according to the new control patterns (S271).

As another example, if in operation S230, the ground shape determining unit 1413 determines that the width of the area of the comparison ground is larger than the desired value, a direction of the reference ground and a direction of the comparison ground may be compared with each other, and the ground shape determining unit 1413 may determine whether the direction of the reference ground and the direction of the comparison ground are parallel to each other (S240). The ground shape determining unit 1413 may obtain coefficients of equations of the reference ground and the comparison ground using the RANSAC algorithm, and utilize the coefficients to compare the direction of the reference ground with the direction of the comparison ground.

If the direction of the reference ground and the direction of the comparison ground are different from each other and the reference ground is a flatland, the ground shape determining unit 1413 may determine that the comparison ground is inclination ground (S241). If the direction of the reference ground and the direction of the comparison ground are different from each other and the reference ground is an inclination ground, the ground shape determining unit 1413 may determine that the comparison ground is inclination ground or flatland ground. The inclination ground may be an uphill inclination or a downhill inclination. Subsequently, the control pattern determining unit 1414 may determine new control patterns for walking on the inclination ground according to a gradient of the extracted comparison ground (S270) and the control signal generating unit 1415 may generate control signals to control the walk-assistive robot 1 according to the new control patterns (S271).

If the direction of the reference ground and the direction of the comparison ground are the same, the ground shape determining unit 1413 may determine whether a height of the reference ground and a height of the comparison ground are the same (S250). If the direction of the reference ground and the direction of the comparison ground are the same and the height of the reference ground and the height of the comparison ground are different from each other, the ground shape determining unit 1413 may determine that the comparison ground is stair ground (S251). When the ground shape determining unit 1413 determines that the comparison ground is stair ground (251), if a position of the reference ground is higher than a position of the comparison ground, the comparison ground may be determined as downhill stair ground. In contrast, if the position of the reference ground is lower than the position of the comparison ground, the comparison ground may be determined as uphill stair ground. Then, the control pattern determining unit 1414 may determine new control patterns for walking on the stair ground according to a width of each stair or a height between the stairs (S270) and the control signal generating unit 1415 may generate control signals to control the walk-assistive robot 1 according to the new control patterns (S271).

If the direction of the reference ground and the direction of the comparison ground are the same and the position of the reference ground and the height of the comparison ground are the same, the reference ground and the comparison ground may be determined as the same ground in which there is no change in gradient (S260). Since the reference ground and the comparison ground are the same ground in which there is no change in gradient, the control pattern determining unit 1414 may not need to obtain new control patterns. Thus, the control signal generating unit 1415 may generate a control signal to control the walk-assistive robot 1 according to existing control patterns (S261).

The aforementioned control operations S210 through S271 may be continuously repeated until the wearer of walk-assistive robot 1 stops moving (S280).

As described above, in a walk-assistive robot and a method of controlling the same according to the one or more example embodiments, even when a surrounding walking environment changes, the walk-assistive robot can rapidly respond to the changes in the surrounding walking environment. Therefore, resistance that a wearer feels with respect to the walk-assistive robot caused by force or pressure applied by the walk-assistive robot may be reduced.

In addition, the wearer who uses the walk-assistive robot can walk naturally even along varying ground. In addition, in the walk-assistive robot and the method of controlling the same according to the one or more example embodiments, the wearer who uses the walk-assistive robot can walk safely even when there is an obstacle, such as unevenness on ground, or even when the ground is particular ground such as stairs or an inclination.

Furthermore, the wearer of the walk-assistive robot can be assisted without feeling resistance with respect to the walk-assistive robot so that the wearer can walk more conveniently.

In addition to controlling an amount of assistance provided to a wearer of the walk-assistive robot based on changes in the terrain, the controller 14 may control the amount of assistance provided to the wearer based on a weight of the wearer. For example, the controller 14 may measure a weight of the wearer using the pressure sensor installed at one or more of the footrest portions 42a and 42b, and adjust the amount of assistance provided to the wearer via the walk assistive robot 1 based on the sensed weight. The sensed weight may include an object that the wearer is holding.

Further still, the controller 14 may provide a different amount of assistance the wearer as the wearer moves though various phases of a walking cycle. For example, the controller 14 may instruct the walk assistive robot 1 to increase an assistance torque applied to a leg of the wearer, if an associated joint is exerting positive work on the leg, for example, when the user is increasing a pace of walking on a flat surface, a sloped surface or a stepped surface. Likewise, the controller 14 may instruct the walk assistive robot 1 to increase a damping torque applied to a leg of the wearer, if an associated joint is exerting negative work on the leg, for example, when the user is decreasing a pace of walking on the flat surface, the sloped surface or the stepped surface.

Although a few example embodiments have been shown and described, i those skilled in the art will appreciate that changes may be made to these example embodiments without departing from the principles and spirit thereof, the scope of which is defined in the claims and their equivalents.

For example, while example embodiments have been described with relation to a walk-assistive robot for a human, one of ordinary skill in the art will appreciate that the example embodiments may be applied to provide walk-assistance to various beings.

What is claimed is:

1. A method of controlling a walk-assistive robot, the method comprising:
    obtaining, via a sensor, a ground data regarding a terrain;
    creating, via a controller, ground information based on the ground data, the ground information including information associated with both a reference ground terrain and a comparison ground terrain located in at least two of a forward direction, a rearward direction, and a sideward direction with respect to a walking direction of the walk-assistive robot;
    determining, via the controller, which of a plurality of ground shapes represents the terrain such that the controller determines that the comparison ground terrain is one of uneven ground, stair ground and inclination ground by analyzing differences between the comparison ground terrain and the reference ground terrain;
    determining, via the controller, a control patterns of the walk-assistive robot by analyzing the ground information such that the controller determines the control patterns of the walk-assistive robot according to the determined ground shape; and
    controlling, via the controller, the walk-assistive robot based on the determined control patterns such that an amount of assistance provided by the walk-assistive robot varies based on the terrain.

2. The method of claim 1, wherein the creating the ground information comprises:
    creating a map regarding the terrain based on the ground data.

3. The method of claim 2, wherein the creating the map includes generating the map by synthesizing the ground data.

4. The method of claim 1, wherein the obtaining of the ground information further comprises:
    calculating a ego-motion associated with the sensor.

5. The method of claim 1, wherein the plurality of ground shapes include one or more of a flatland ground, an uphill inclination ground, a downhill inclination ground, an uphill stair ground, a downhill stair ground, and an obstacle ground.

6. The method of claim 1, wherein the determining which of the plurality of ground shapes represents the terrain comprises:
    determining the reference ground terrain and the comparison ground terrain; and
    determining which of the plurality of ground shapes represents the terrain by,
    determining that the comparison ground terrain is uneven ground, if a size of the comparison ground terrain is smaller than a desired value,
    determining that the comparison ground terrain is stair ground, if a direction of the reference ground terrain is parallel to a direction of the comparison ground terrain and a height of the reference ground terrain is different from a height of the comparison ground terrain, and
    determining the comparison ground terrain as inclination ground, if the direction of the reference ground terrain is different from the direction of the comparison ground terrain.

7. A walk-assistive robot configured to navigate a terrain, the walk-assistive robot comprising:
    a sensor configured to collect ground data regarding the terrain,
    a controller configured to,
        create ground information regarding the terrain based on the ground data, the ground data including information associated with both a reference ground terrain and a comparison ground terrain located in at least two of a forward direction, a rearward direction, and a sideward direction with respect to a walking direction of the walk-assistive robot,
        determine which of a plurality of ground shapes represents the terrain such that the controller determines that the comparison ground terrain is one of uneven ground, stair ground and inclination ground by analyzing differences between the comparison ground terrain and the reference ground terrain, determine a control patterns of the walk-assistive robot by analyzing the ground information such that the controller determines the control patterns of the walk-assistive robot according to the determined ground shape, and control the walk-assistive robot based on the determined control patterns such that an amount of assistance provided by the walk-assistive robot varies based on the terrain.

8. The walk-assistive robot of claim 7, wherein the controller is configured to create the ground information by generating a map regarding the terrain based on the ground data.

9. The walk-assistive robot of claim 8, wherein the controller is configured to generate the map by synthesizing the ground data.

10. The walk-assistive robot of claim 7, wherein the controller is configured to calculate an ego-motion associated with the sensor.

11. The walk-assistive robot of claim 7, wherein the plurality of ground shapes include one or more of a flatland ground, an uphill inclination ground, a downhill inclination ground, an uphill stair ground, a downhill stair ground, and an obstacle ground.

12. The walk-assistive robot of claim 7, wherein the controller is configured to determine which of the plurality of ground shapes represents the terrain by, determining that the comparison ground terrain is uneven ground, if a size of the comparison ground terrain is smaller than a desired value, determining that the comparison ground terrain is stair ground, if a direction of the reference ground terrain is parallel to a direction of the comparison ground terrain and a height of the reference ground terrain is different from a height of the comparison ground terrain, and determining the comparison ground terrain is inclination ground, if the direction of the reference ground terrain is different from the direction of the comparison ground terrain.

13. A walk-assistive robot configured to navigate a terrain, the walk-assistive robot comprising:

a sensor configured to receive a ground information, the ground information including information on the terrain, the ground information including information associated with both a reference ground terrain and a comparison ground terrain located in at least two of a forward direction, a rearward direction, and a sideward direction with respect to a walking direction of the walk-assistive robot; and a controller configured to, determine which of a plurality of ground shapes represents the terrain such that the controller determines that the comparison ground terrain is one of uneven ground, stair ground and inclination ground by analyzing differences between the comparison ground terrain and the reference ground terrain, determine a control patterns of the walk-assistive robot by analyzing the ground information such that the controller determines the control patterns of the walk-assistive robot according to the determined ground shape, and control the walk-assistive robot based on the determined control patterns such that an amount of assistance provided by the walk-assistive robot varies based on the terrain.

* * * * *